(12) United States Patent
Snepvangers

(10) Patent No.: US 12,033,274 B2
(45) Date of Patent: Jul. 9, 2024

(54) SYSTEMS AND METHODS FOR MODELING REALISTIC EYE COLOR

(71) Applicant: TRANSFOLIO, LLC, Irving, TX (US)

(72) Inventor: Jeroen Snepvangers, Van Nuys, CA (US)

(73) Assignee: TRANSFOLIO, LLC, Irving, TX (US)

( * ) Notice: Subject to any disclaimer, the term of this patent is extended or adjusted under 35 U.S.C. 154(b) by 184 days.

(21) Appl. No.: 17/895,767

(22) Filed: Aug. 25, 2022

(65) Prior Publication Data
US 2023/0090662 A1 Mar. 23, 2023

Related U.S. Application Data

(60) Provisional application No. 63/237,674, filed on Aug. 27, 2021.

(51) Int. Cl.
| | | |
|---|---|---|
| G06T 15/50 | (2011.01) | |
| G06T 15/06 | (2011.01) | |
| G06T 17/20 | (2006.01) | |
| G06T 19/20 | (2011.01) | |

(52) U.S. Cl.
CPC ........... *G06T 15/506* (2013.01); *G06T 15/06* (2013.01); *G06T 17/20* (2013.01); *G06T 19/20* (2013.01); *G06T 2219/2004* (2013.01)

(58) Field of Classification Search
CPC ....... G06T 15/06; G06T 15/506; G06T 17/20; G06T 19/20; G06T 2219/2004
See application file for complete search history.

(56) References Cited

U.S. PATENT DOCUMENTS

| | | |
|---|---|---|
| 9,456,772 B2 | 10/2016 | Cameron |
| 11,074,675 B2 | 7/2021 | Cao |
| 2016/0005210 A1* | 1/2016 | Borodavka ............. G06T 15/06 |
| | | 345/419 |
| 2018/0012392 A1* | 1/2018 | Kryachko ............. G06T 15/005 |
| 2018/0012401 A1 | 1/2018 | Bérard et al. |
| 2019/0142940 A1 | 5/2019 | Kambiz |
| 2019/0156526 A1* | 5/2019 | Liu ........................ G06T 7/0012 |
| 2020/0273239 A1* | 8/2020 | Halén ..................... G06T 15/60 |

OTHER PUBLICATIONS

Extended Search Report for related International Application No. 20755654.9; action dated Oct. 17, 2022; (8 pages).
Shu, et al.; Monte Carlo investigation on quantifying the retinal pigment epithelium melanin concentration by photoacoustic ophthalmoscopy; Journal of Biomedical Optics; Oct. 2015; (10 pages).
International Preliminary Report on Patentability for related International Application No. PCT/US2022/041685; action dated Feb. 27, 2024; (9 pages).

* cited by examiner

*Primary Examiner* — Ming Wu
(74) *Attorney, Agent, or Firm* — K&L Gates LLP

(57) ABSTRACT

The present disclosure provides new and innovative systems and methods for generating eye models with realistic color. In an example, a computer-implemented method includes obtaining refraction data, obtaining mesh data, generating aligned model data by aligning the refraction data and the mesh data, calculating refraction points in the aligned model data, and calculating an approximated iris color based on the refraction points and the aligned model data by calculating melanin information for the aligned model data based on the refraction points for iris pixels in the aligned model data.

17 Claims, 21 Drawing Sheets

*If at ABL boundary coming from AH:*
  *If (FresnelTest) = Reflect), then*
*Function(RayCompleted)*   #specular reflection back to the camera
*NewRayStarts*
else
 *CurrentLayer = ABL*    #ray enters ABL
 $v_d = Function(DiffusePerturbation)$   #vector $v_d$ is the new direction
 $l_{bb} = \frac{h_{ABL}}{\cos\alpha}$ = length of straight line from current boundary to next boundary along $v_d(\alpha,\beta)$

*If at ABL boundary coming from ABL:*
    *If (FresnelTest) = Reflect), then*
*CurrentLayer = ABL*    #ray reflects back into ABL
$v_d = Function(DiffusePerturbation)$   #vector $v_d$ is the new direction
$l_{bb} = \frac{h_{ABL}}{\cos\alpha}$ = length of straight line from current boundary to next boundary along $v_d(\alpha,\beta)$
              *else*
*Function(RayCompleted)*   #ray transmits to the camera
*NewRayStarts*

*If at Stromal boundary coming from ABL:*
    *If (FresnelTest) = Reflect), then*
*CurrentLayer = ABL*    #ray reflects back into ABL
$v_d = Function(DiffusePerturbation)$   #vector $v_d$ is the new direction
$l_{bb} = \frac{h_{ABL}}{\cos\alpha}$ = length of straight line from current boundary to next boundary along $v_d(\alpha,\beta)$
              *else*
*CurrentLayer = Stroma*     #ray enters Stroma
$v_d = Function(DiffusePerturbation)$   #vector $v_d$ is the new direction
$l_{bb} = \frac{h_{STROMA}}{\cos\alpha}$ = length of straight line from current boundary to next boundary along $v_d(\alpha,\beta)$
   *If at Stromal boundary coming from Stroma:*
    *If (FresnelTest) = Reflect), then*
*CurrentLayer = Stroma*     #ray reflects back into Stroma
$v_d = Function(DiffusePerturbation)$   #vector $v_d$ is the new direction
$l_{bb} = \frac{h_{STROMA}}{\cos\alpha}$ = length of straight line from current boundary to next boundary along $v_d(\alpha,\beta)$
              *else*
*CurrentLayer = ABL*     #ray enters ABL
$v_d = Function(DiffusePerturbation)$   #vector $v_d$ is the new direction
$l_{bb} = \frac{h_{ABL}}{\cos\alpha}$ = length of straight line from current boundary to next boundary along $v_d(\alpha,\beta)$

*If at IPE boundary coming from Stroma:*
    *If (FresnelTest) = Reflect), then*
*CurrentLayer = Stroma*     #ray reflects back into Stroma
$v_d = Function(DiffusePerturbation)$   #vector $v_d$ is the new direction
$l_{bb} = \frac{h_{STROMA}}{\cos\alpha}$ = length of straight line from current boundary to next boundary along $v_d(\alpha,\beta)$
              *else*
*NewRayStarts*       #ray is absorbed and ends\

*If (re)entering the ABL Layer:*
          *If* $(AbsorbTest(l_{bb}, i, j)) = Yes)$, *then*
  *NewRayStarts*          #ray ends and new ray starts
                *else*
  *GoToNextBoundary(v)*      #ray travels along v to next boundary
  *For all pixels(i, j) along* $l_{bb}$    #all pixels that ray traversed along line $l_{bb}$
    *TallyDistancePerPixel(i, j)*   #Tally the distance ray travels in pixel(i,j)

*If (re)entering the Stromal Layer:*
          *If (AttenuationTest) = Absorb), then*
  *NewRayStarts*          #ray ends and new ray starts
                *else*

*If (AttenuationTest) = Transmit), then*

*GoToNextBoundary(v)*      #ray travels along v to next boundary
  *For all pixels(i, j) along* $l_{bb}$    #all pixels that ray traversed along line $l_{bb}$
    *TallyDistancePerPixel(i, j)*   #Tally the distance ray travels in pixel(i,j)

*else*                 #AttenuationTest = "Scatter"

Determine a random location along $l_{bb}$ as the scatter location and then move there
  *ScatterPos* $= u_{10} \cdot l_{bb}$ Tally all the distances per pixel up to the scatter location
  *For all pixels(i, j) along* $l_{bb}$ *to ScatterPos*  #all pixels that ray traversed to scatter
    *TallyDistancePerPixel(i, j)*  #Tally the distance ray travels in pixel(i,j)

```
Loop until u_8 ≤ 0.5 · (1 + cos²α_R)      # only accept if phase function holds
    u_7 = random[0,1]                      # choose new random number
    u_8 = random[0,1]                      # choose new random number
    α_R = 2π · u_7                         # new polar angle after scatter
    β_R = 2π · u_8                         # new azimuthal angle after scatter GoToNextBoundary(v)                        #ray travels along v to next boundary
For all pixels(i,j) along l_bb             #all pixels that ray traversed along line l_bb
    TallyDistancePerPixel(i,j)             #Tally the distance ray travels in pixel(i,j)
```

```
# length that ray traveled inside pixel(i,j)
                    let l_pixel = Pythagoras(VectorExitsPixel(i,j) - VectorEntersPixel(i,j))
                                 If (CurrentLayer = ABL), then
    l_A(i,j) = l_A(i,j) + l_pixel    #Tally ABL length traveled in (i,j)
                                      else
    l_S(i,j) = l_S(i,j) + l_pixel    #Tally Stromal length traveled in (i,j)
```

FIG. 13D

SYSTEMS AND METHODS FOR MODELING REALISTIC EYE COLOR

CROSS-REFERENCE TO RELATED APPLICATIONS

The instant application claims priority to U.S. Provisional Patent Application No. 63/237,674, entitled "Systems and Methods for Modeling Realistic Eye Color" and filed Aug. 27, 2021, the disclosure of which is hereby incorporated by reference in its entirety.

TECHNICAL FIELD

The instant application relates to image data processing and more specifically to three-dimensional modeling.

BACKGROUND

Eyes are an organ that reacts to light and allows vision. Light enters the eye through the cornea, through the pupil and then through the lens. The lens shape is changed for near focus (accommodation) and is controlled by the ciliary muscle. Cells within the eye are able to detect visible light and convey this information to the brain by converting the light into electrical signals that are transmitted to the brain. The brain interprets these electrical signals as sight and vision.

SUMMARY

The present disclosure provides new and innovative systems and methods for generating eye models with realistic color. In an example, a computer-implemented method includes obtaining refraction data, obtaining mesh data, generating aligned model data by aligning the refraction data and the mesh data, calculating refraction points in the aligned model data, and calculating an approximated iris color based on the refraction points and the aligned model data by calculating melanin information for the aligned model data based on the refraction points for iris pixels in the aligned model data.

In an example, the computer-implemented method includes calculating a color of the iris based on a melanin absorption coefficient, an iris stroma scattering coefficient, and an anisotropy of a scattering phase function.

In an example, the computer-implemented method includes calculating the refraction points based on multiple lighting conditions.

In an example, a computer-implemented method includes obtaining refraction data, obtaining mesh data, generating aligned model data by aligning the refraction data and the mesh data, calculating refraction points in the aligned model data, and calculating an approximated iris color based on the refraction points and the aligned model data by calculating a Mie scattering.

Additional features and advantages of the disclosed method and apparatus are described in, and will be apparent from, the following detailed description and the figures. The features and advantages described herein are not all-inclusive and, in particular, many additional features and advantages will be apparent to one of ordinary skill in the art in view of the figures and detailed description. Moreover, it should be noted that the language used in the specification has been principally selected for readability and instructional purposes, and not to limit the scope of the inventive subject matter.

BRIEF DESCRIPTION OF THE FIGURES

The description will be more fully understood with reference to the following figures, which are presented as exemplary aspects of the disclosure and should not be construed as a complete recitation of the scope of the disclosure, wherein:

FIGS. 13A-D are conceptual illustrations of pseudocode for a variety of functions in example aspects of the present disclosure.

DETAILED DESCRIPTION

Figure 1:
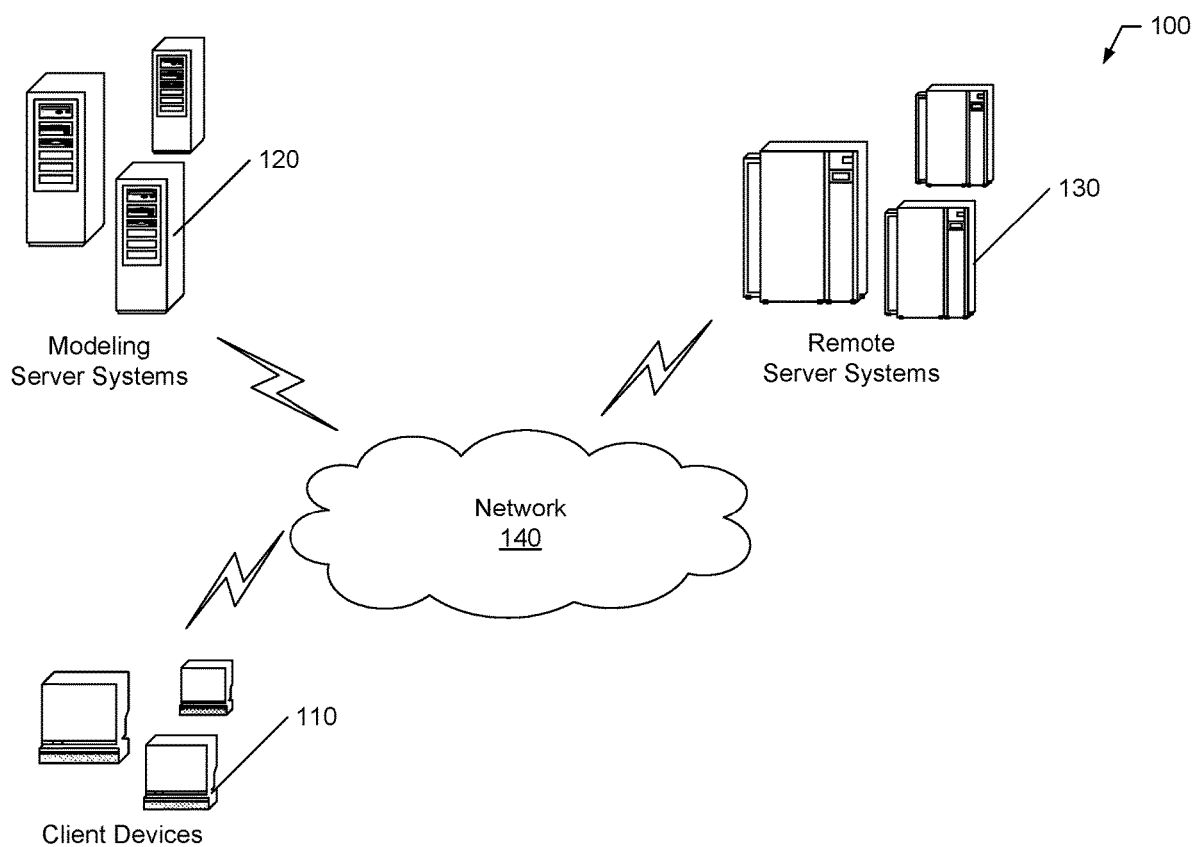
FIG. 1 illustrates a block diagram of an operating environment according to an example aspect of the present disclosure.

Turning now to the drawings, techniques are disclosed for new and innovative systems and methods for generating eye models with realistic color. In computer graphics, a variety of techniques exist for capturing humans and reproducing them as realistically and as accurately as possible in a three-dimensional (3D) virtual environments. A computer-generated human model that accurately represents its real-life counterpart is often referred to as a digital double or a digital human. Capturing and reproducing humans realistically includes (1) capturing and reproducing the geometric shape of the human and (2) capturing and reproducing organic tissue. These two parts are interdependent as shape can influence the appearance of the tissue and vice versa. Capturing the geometric shape can include obtaining the anterior shape of a fixated human subject. The geometry can be reproduced in a computer-generated model including vertices and normal vectors of a polygonal approximation of the shape, which can include a triangular or rectangular mesh. By capturing two or more fixated shapes, also called blend shapes, movements in the computer-generated model can be reproduced by interpolating between the two shapes. Capturing the optical properties of the organic tissue is more complex. For estimating the color of organic tissue, a variety of parameters should be considered in order to accurately model how the tissue interacts with light sources. These parameters include, but are not limited to, light absorption, reflection, refraction, and scattering. By imaging the tissue in controlled lighting environments and camera positions, the fundamental parameters that control how a tissue behaves in real-world conditions can be modeled. The parameters can include, but are not limited to, the shape and the optical properties of the eyes, such as light reflectivity, light absorption, and light scattering. The computer-generated model can be used to accurately represent the tissue in any computer-generated lighting environment and camera position.

Recently, progress has been made in capturing and reproducing skin. In particular, the process of capturing (and separating) the specular reflectivity and sub-surface scattering of skin have been captured successfully due to the polarity preservation of specular reflectivity in contrast with loss of initial polarity of scattering photons in the epidermal. Similarly, much progress has been made with capturing and analyzing the optical properties of skin by means of collimated light, such as lasers. However, these existing techniques typically are not successful at accurately modeling other features of the human body, such as eyes. For example, existing skin capture techniques using polarized filters do not transfer well to determining the color and optical behavior of the iris as most photons that enter the eye through the cornea will be either absorbed or scattered before they exit the eye towards an observer. Therefore, by the time the photons reach the iris, the scattering will have altered the photons' polarization and hence, the polarized filters used in the skin capture techniques fail to capture useful information. Moreover, specular reflection typically appears as white Purkinje reflections off the cornea and lens. Similarly, other scanning techniques, such as with collimated light sources (e.g. lasers), cannot be safely used to scan eyes without risking the health and safety of the eyes. Accordingly, new techniques are needed to realistically model eyes for computer-generated environments.

System and methods in accordance with embodiments of the invention allow for accurate and realistic modeling of eyes, particularly in the modeling and reproduction of iris colors. By capturing data regarding a human eye in a controlled lighting environment and from a variety of camera positions, the shape and composition of the eye can be determined. This data allows accurate models to be generated that reproduce a realistic likeness of the eyes' color and optical behavior in a computer-generated environment. In particular, the color of the iris is a highly complex optical phenomenon requiring understanding of the anatomy, refraction of the cornea (as well as aqueous humor and iris' stroma), the absorption by eumelanin and pheomelanin molecules, scattering by the iris' stroma, and the behavior of photons as they pass through the anterior chamber. In particular, photons that travel through the cornea to the iris experience refraction absorption, reflection, and scattering. These optical phenomena are extremely complex and interdependent, which make them difficult to accurately model. However, a variety of information regarding the properties of an eye can be used to approximate the data needed to accurately model the eye. For example, the amount and type of absorption can be dependent on the photon's wavelength, the amount of melanin in the melanosomes (which can be dependent on the productivity of melanocytes), and/or the type of melanin in the melanosomes. The amount of scatter can be dependent on the photon's wavelength, the distance travelled through the stroma (which is dependent on the iris' stroma), the scattering phase function or anisotropy (which is dependent on scatterer's size and structure), and/or the incident and exiting angle of the photon when entering and exiting the iris. The amount of reflection (and iris ambient occlusion) can be dependent on a surface normal vector of the cornea (for Purkinje specular reflections) and/or a surface normal vector of the iris stroma (for iris specular and ambient occlusion). As described in more detail herein, models can include absorption coefficients ($\mu_a$), scatter coefficients ($\mu_s$), and anisotropy coefficients (g) along with independent modeling of specular and ambient occlusion from the scattering and absorption in the iris.

The modeling devices and processes described herein provide and improvement over existing techniques for determining eye color and generating accurate computer models. In particular, the modeling devices and processes are an improvement in computer-related technology and technological processes by allowing computing device to produce accurate and realistic eye models that can be utilized in a variety of contexts, including generating computer models. Additionally, the modeling devices and processes allow for the automation of modeling eyes that previously could not be automated.

A variety of computing systems and processes for generating eye models with realistic color in accordance with aspects of the disclosure are described in more detail herein.

Operating Environments and Computing Devices

FIG. 1 illustrates a block diagram of an operating environment 100 in accordance with one or more aspects of the present disclosure. The operating environment 100 can include client devices 110, modeling server systems 120, and/or remote server systems 130 in communication via network 140. In many aspects, the modeling server systems 120 and/or remote server systems 130 are implemented using a single server. In a variety of aspects, the modeling server systems 120 and/or remote server systems 130 are implemented using a plurality of servers. In several aspects, client devices 110 are implemented utilizing the modeling server systems 120 and/or remote server systems 130. In a variety of aspects, modeling server systems 120 and/or remote server systems 130 are implemented using the client devices 110.

Client devices 110 can obtain and/or generate a variety of data, such as images and/or scans of eyes, as described herein. Modeling server systems 120 obtain data regarding one or more eyes and generate models of the eyes as described herein. The modeling server system 120 can also provide modeling data to a variety of remote server systems 130. In a variety of embodiments, the modeling server system 120 provides modeling data for integration into computer-generated models. In a number of embodiments, the modeling server system 120 provides middleware or other computer software than can be used by remote server systems 130 to generate, incorporate, and/or manipulate eye models as described herein. Remote server systems 130 can obtain and provide modeling data as described herein. The network 140 can include a LAN (local area network), a WAN (wide area network), telephone network (e.g. Public Switched Telephone Network (PSTN)), Session Initiation Protocol (SIP) network, wireless network, point-to-point network, star network, token ring network, hub network, wireless networks (including protocols such as EDGE, 3G, 4G LTE, Wi-Fi, 5G, WiMAX, and the like), the Internet, and the like. A variety of authorization and authentication techniques, such as username/password, Open Authorization (OAuth), Kerberos, SecureID, digital certificates, and more, may be used to secure the communications. It will be appreciated that the network connections shown in the operating environment 100 are illustrative, and any means of establishing one or more communications links between the computing devices may be used.

Figure 2:
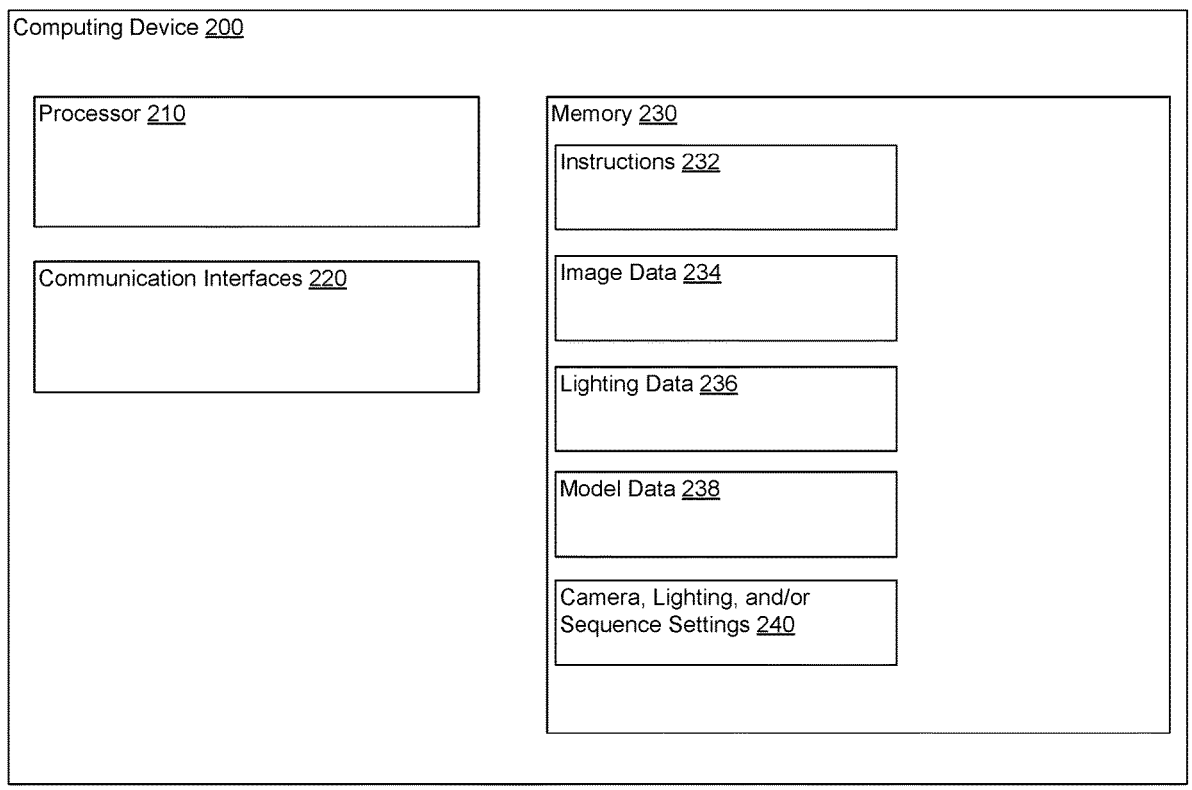
FIG. 2 illustrates a block diagram of a computing device according to an example aspect of the present disclosure.

Any of the computing devices shown in FIG. 1 (e.g. client devices 110, modeling server systems 120, and/or remote server systems 130) can include a single computing device, multiple computing devices, a cluster of computing devices, and the like. A conceptual illustration of a computing device in accordance with an embodiment of the invention is shown in FIG. 2. The computing device 200 includes a processor 210 in communication with memory 230. The computing device 200 can also include one or more communication interfaces 220 capable of sending and receiving data. In a number of embodiments, the communication interface 220 is in communication with the processor 210 and/or the memory 230. In several embodiments, the memory 230 is any form of storage storing a variety of data, including, but not limited to, instructions 232, image data 234, lighting data 236, and/or model data 238. In many embodiments, instructions 232, image data 234, lighting data 236, and/or model data 238 are stored using an external server system and received by the computing device 200 using the communications interface 220. The processor 210 can be directed, by the instructions 232, to perform a variety of model generation processes based on the image data 234, lighting data 236, and/or model data 238 as described herein.

The processor 210 can include one or more physical processors communicatively coupled to memory devices, input/output devices, and the like. As used herein, a processor may also be referred to as a central processing unit (CPU). Additionally, as used herein, a processor can include one or more devices capable of executing instructions encoding arithmetic, logical, and/or I/O operations. In one illustrative example, a processor may implement a Von Neumann architectural model and may include an arithmetic logic unit (ALU), a control unit, and a plurality of registers. In many aspects, a processor may be a single core processor that is typically capable of executing one instruction at a time (or process a single pipeline of instructions) and/or a multi-core processor that may simultaneously execute multiple instructions. In a variety of aspects, a processor may be implemented as a single integrated circuit, two or more integrated circuits, and/or may be a component of a multi-chip module in which individual microprocessor dies are included in a single integrated circuit package and hence share a single socket.

Memory 230 can include a volatile or non-volatile memory device, such as RAM, ROM, EEPROM, or any other device capable of storing data. Communication devices 220 (e.g. input/output devices) can include a network device (e.g., a network adapter or any other component that connects a computer to a computer network), a peripheral component interconnect (PCI) device, storage devices, disk drives, sound or video adaptors, photo/video cameras, printer devices, keyboards, displays, etc.

Although specific architectures for computing devices in accordance with embodiments of the invention are conceptually illustrated in FIG. 2, any of a variety of architectures, including those that store data or applications on disk or some other form of storage and are loaded into memory at runtime, can also be utilized. Additionally, any of the data utilized in the system can be cached and transmitted once a network connection (such as a wireless network connection via the communications interface) becomes available. In several aspects, the computing device 200 provides an interface, such as an API or web service, which provides some or all of the data to other computing devices for further processing. Access to the interface can be open and/or secured using any of a variety of techniques, such as by using client authorization keys, as appropriate to the requirements of specific applications of the disclosure. In a variety of embodiments, a memory includes circuitry such as, but not limited to, memory cells constructed using transistors, that store instructions. Similarly, a processor can include logic gates formed from transistors (or any other device) that dynamically perform actions based on the instructions stored in the memory. In several embodiments, the instructions are embodied in a configuration of logic gates within the processor to implement and/or perform actions described by the instructions. In this way, the systems and methods described herein can be performed utilizing both general-purpose computing hardware and by single-purpose devices.

Modeling Eyes with Accurate Colors

Generating a model of an eye can include generating a three-dimensional mesh of the anterior surface of the eye, including the sclera, limbus, and/or cornea. In a variety of embodiments, a camera can project one or more projections, projected from one or more angles, onto a fluorescein tinted tear film. These projections can be captured by a coaxial telecentric photographic sensor. The captured projections can be transformed into a three-dimensional mesh of the surface of the object (e.g. eye) being imaged. For example, each measured point of the projections can be mapped to a vertex in the three-dimensional mesh. In a number of embodiments, the three-dimensional mesh is accurate to within 10 microns of the object being imaged. The normal vectors of each vertex and polygon can be calculated based on the three-dimensional mesh using any of a variety of techniques, such as interpolation. In many embodiments, the generated three-dimensional mesh has a capture diameter of approximately 20-25 mm and approximately 500,000 measured points that form the vertices of the mesh. Each vertex can have a measured normal vector. In several embodiments, the camera also captures a near-infrared image of the object (e.g. eye).

Figure 3:
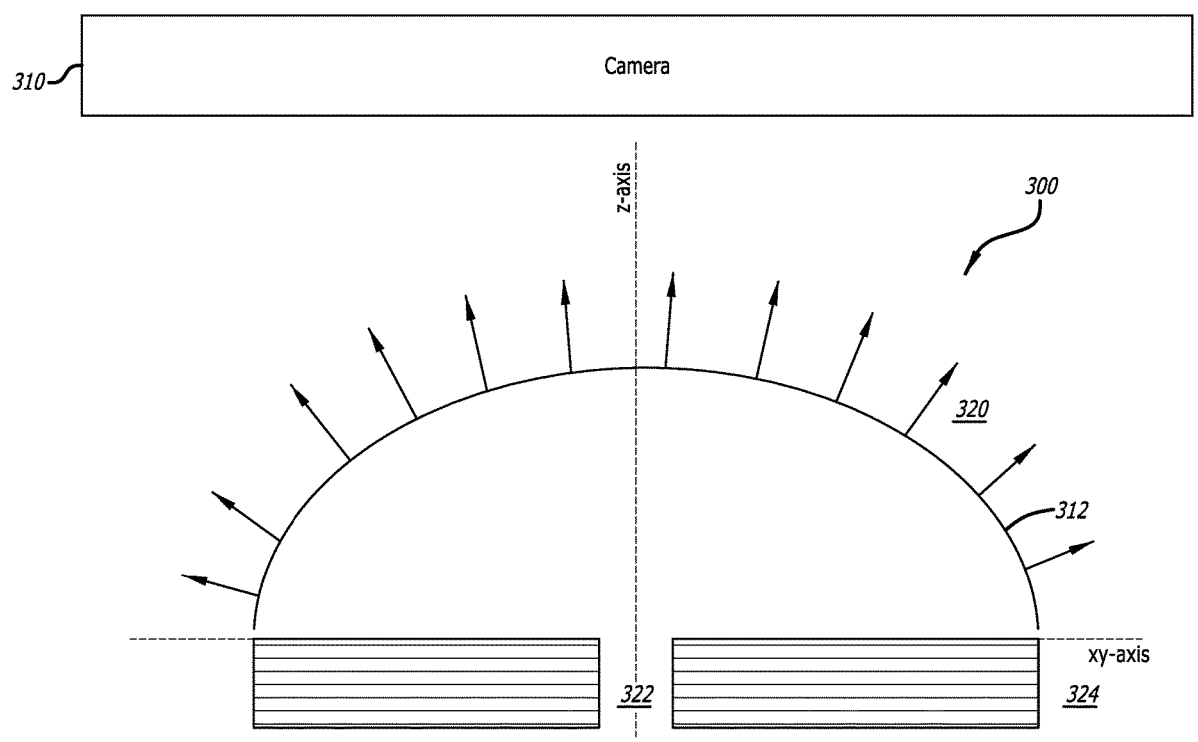
FIG. 3 conceptually illustrates an imaging system according to an example aspect of the present disclosure.

FIG. 3 conceptually illustrates an imaging system according to an example aspect of the present disclosure. The imaging system 300 includes a camera 310 and an eye 312. It should be noted that the imaging system 300 includes cameras, infrared imagers, and/or any other device capable of generating an image of the eye 312 as described herein. The eye 312 includes a cornea 320, a pupil 322, and an iris 324. The camera 310 can be aligned perpendicular to the eye 312 and located approximately aligned to the cornea 320, such as along a z-axis as shown in FIG. 3. However, it should be noted that a variety of orientations of the imaging system relative to the eye (or any other object) can be utilized as appropriate.

Generating accurate eye models can also include capturing the texture of the eye including, but not limited to, the color and optical properties of the eye. In several embodiments, the texture of the eye can be generated based on image data captured using one or more imaging sensors oriented coaxial to an eye fixation point along with one or more lights, with at least one of the lights coaxial to at least one of the imaging sensors. In many embodiments, the imaging sensor includes a red-green-blue (RGB) sensor with a red peak of approximately 600 nm, a green peak of approximately 520 nm, and a blue peak of approximately 460 nm. The imaging sensor(s) can be located behind an optical lens system. In several embodiments, the other lights are positioned at various angles from temporal, nasal, superior, and inferior sides (e.g. left, right, up, down) of the eye. The angle to the optical axis can be measured for each light. The generated image sequence can include a strobe sequence of images from the different lights. In a number of embodiments, there are five images in the image sequence, with one image being captured for each light in the imaging system. In a variety of embodiments, the image sequence can be repeated one or more times to correct any possible optical flow (e.g. small movements) of the subject and/or the eye during the capture sequence. In addition to capturing the image sequence, a color chart can also be captured using the same strobe sequence with the same lights at the same angles and distances. The color chart can be used to normalize differences in intensities of the lights for each wavelength (e.g. perform color correction). A variety of devices and techniques for capturing images, including imaging the texture of an eye, are disclosed in PCT International Patent Application No. PCT/US2020/058575, titled "Coaxial Multi-Illuminated Ocular Imaging Apparatus" and filed Nov. 2, 2020, the disclosure of which is hereby incorporated by reference in its entirety.

The image sequence can include one or more (e.g. five) images of the coaxially fixated eye, illuminated from one or more (e.g. five) different angles in incidence, $\theta_z$, where the z-axis can be defined as the coaxial lens axis and the x-y plane is parallel to the eye's iris plane and perpendicular to the coaxial lens axis. The following can be defined for the x-y plane:

- $\theta_{xy}=0°$ for nasal illumination for right (OD) eye and temporal illumination for left (OS) eye (e.g. light coming from the left side of the eye)
- $\theta_{xy}=180°$ for temporal illumination for right (OD) eye and nasal illumination for left (OS) eye (e.g. light coming from the right side of the eye)
- $\theta_{xy}=90°$ for superior illumination for right (OD) and left (OS) eyes (e.g. light coming from above the eye)
- $\theta_{xy}=270°$ for inferior illumination for right (OD) and left (OS) eyes (e.g. light coming from below the eye)

In several embodiments, the angle of the lights to the camera axis can be calculated based on a Purkinje reflection (e.g. the first Purkinje reflection) and/or the normal vector angle of the cornea at that point. Purkinje reflections are specular reflections where the angle of the incoming light and the corneal surface normal equals the angle of the reflected light and the corneal surface normal. As the imaging sensor records light that travels parallel to the axis of the lens (e.g. due to the telecentric lens), we can conclude that the angle of the light and the lens axis is two times the angle of the corneal surface normal and the lens axis.

Figure 4:
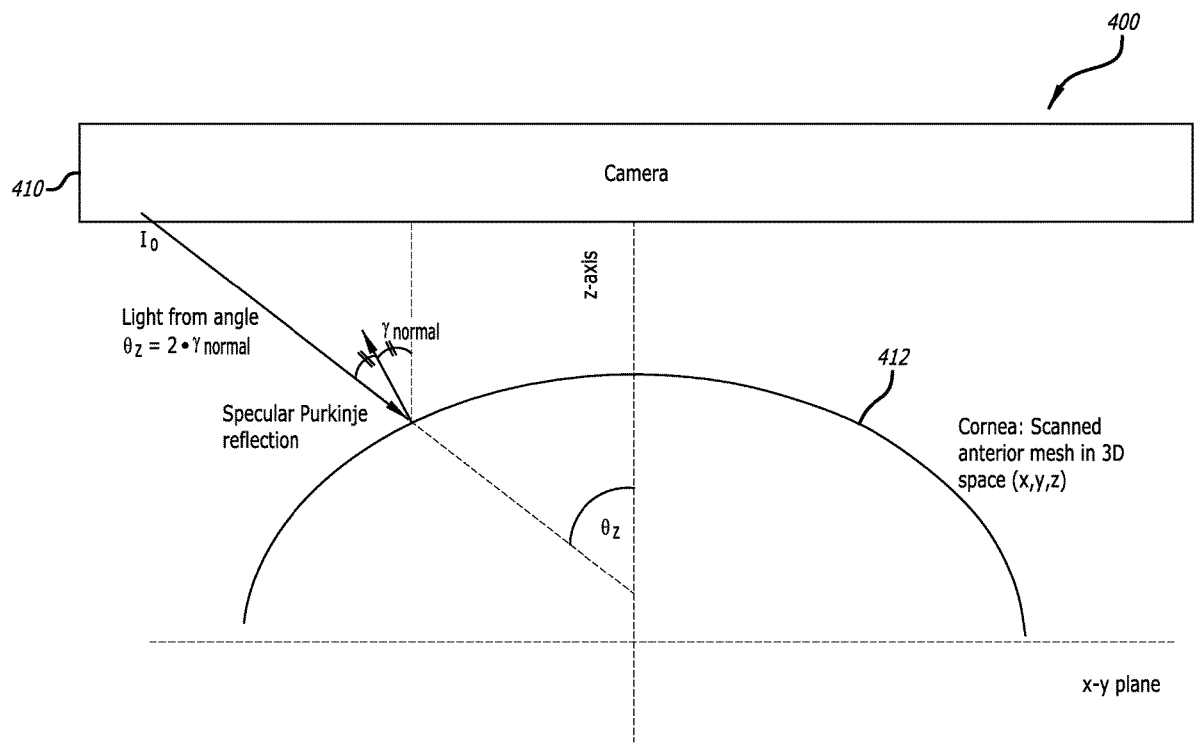
FIG. 4 conceptually illustrates a light angle calculation according to an example aspect of the present disclosure.

FIG. 4 conceptually illustrates a light angle calculation according to an example aspect of the present disclosure. The imaging system 400 includes a camera 410 located coaxially to corneal surface 412. Corneal surface 412 normal $\gamma_{normal}$ is located parallel to the z-axis and light from angle $\theta_z=2*\gamma_{normal}$ intersects camera 410 at light source $I_0$.

Generating a model of the eye can include aligning the three-dimensional mesh and the image sequence along a common reference point. In several embodiments, the common reference point is the iris of the eye. The diameter of the iris can be used to scale the three-dimensional mesh and/or one or more of the images in the image sequence such that the iris is of approximately equal size in each piece of data. In a variety of embodiments, veins in the eye (such as veins in the sclera) can be used as secondary reference points. In particular, as the imaging devices generating the three-dimensional mesh and the image sequence should be telecentric to the eye itself, the images and mesh should exhibit minimal distortion relative to each other and capture the eye at approximately the true size of the eye. The color of the eye can be determined based on the sensor intensity for the imaging devices capturing the three-dimensional mesh and/or the image sequence.

In a variety of embodiments, the intensity I for pixel (n,m) of an imaging sensor can be defined as:

$$I_{n,m} \in \begin{bmatrix} r & g & b \\ \vdots & \vdots & \vdots \\ r & g & b \end{bmatrix}$$

where r, g, and b are intensity functions for red, green, and blue intensities respectively, where $$(r,g,b) \in \{[0,255],[0,255],[0,255]\} \in (\mathbb{N},\mathbb{N},\mathbb{N})$$

and r, g, and i are functions of light angle $\theta$. In many embodiments, $\theta$ is expressed as an addition of angle with z-axis and x-y plane: $\theta_z+\theta_{xy}$, initial intensity $I_0$, and corneal mesh coordinate $c_{n,m} \in (x,y,z)$. In several embodiments, $c_{n,m}$ is the first intersection of perpendicular line from pixel (n,m) to the corneal mesh. In a number of embodiments, $\theta$ is expressed based on the normal vector $\gamma_{n,m}$ at corneal mesh coordinate $c_{n,m}$. The intensity for pixel (n,m) can be expressed as the following matrix, where each row in the matrix corresponds to a captured image:

$$I_{n,m} \rightarrow \begin{bmatrix} r(\theta_{xy}, \theta_z, I_0, c_{n,m}, \gamma_{n,m}) & g(\theta_{xy}, \theta_z, I_0, c_{n,m}, \gamma_{n,m}) & b(\theta_{xy}, \theta_z, I_0, c_{n,m}, \gamma_{n,m}) \\ \vdots & \vdots & \vdots \end{bmatrix}$$

In many embodiments, $\theta_{xy} \in \{0,90,180,270\}$ for the images corresponding to the side lights (e.g. left, right, above, and below images) and $\theta_{xy}=\theta_z=0$ for the images corresponding to the coaxial light (e.g. the coaxial image), $I_{n,m}$ can be expressed as:

$$I_{n,m} \rightarrow$$

$$\begin{bmatrix} r(0, 0, I_0, c_{n,m}, \gamma_{n,m}) & g(0, 0, I_0, c_{n,m}, \gamma_{n,m}) & b(0, 0, I_0, c_{n,m}, \gamma_{n,m}) \\ r(0, \theta_z, I_0, c_{n,m}, \gamma_{n,m}) & g(0, \theta_z, I_0, c_{n,m}, \gamma_{n,m}) & b(0, \theta_z, I_0, c_{n,m}, \gamma_{n,m}) \\ r(90, \theta_z, I_0, c_{n,m}, \gamma_{n,m}) & g(90, \theta_z, I_0, c_{n,m}, \gamma_{n,m}) & b(90, \theta_z, I_0, c_{n,m}, \gamma_{n,m}) \\ r(180, \theta_z, I_0, c_{n,m}, \gamma_{n,m}) & g(180, \theta_z, I_0, c_{n,m}, \gamma_{n,m}) & b(180, \theta_z, I_0, c_{n,m}, \gamma_{n,m}) \\ r(270, \theta_z, I_0, c_{n,m}, \gamma_{n,m}) & g(270, \theta_z, I_0, c_{n,m}, \gamma_{n,m}) & b(270, \theta_z, I_0, c_{n,m}, \gamma_{n,m}) \end{bmatrix} \equiv$$

$$\begin{bmatrix} \text{coaxial} \\ \text{from left } |OD \text{ nasal}| \ OS \text{ temporal} \\ \text{from right } |OD \text{ temporal}| \ OS \text{ nasal} \\ \text{from above} \\ \text{from below} \end{bmatrix}$$

Figure 5A:
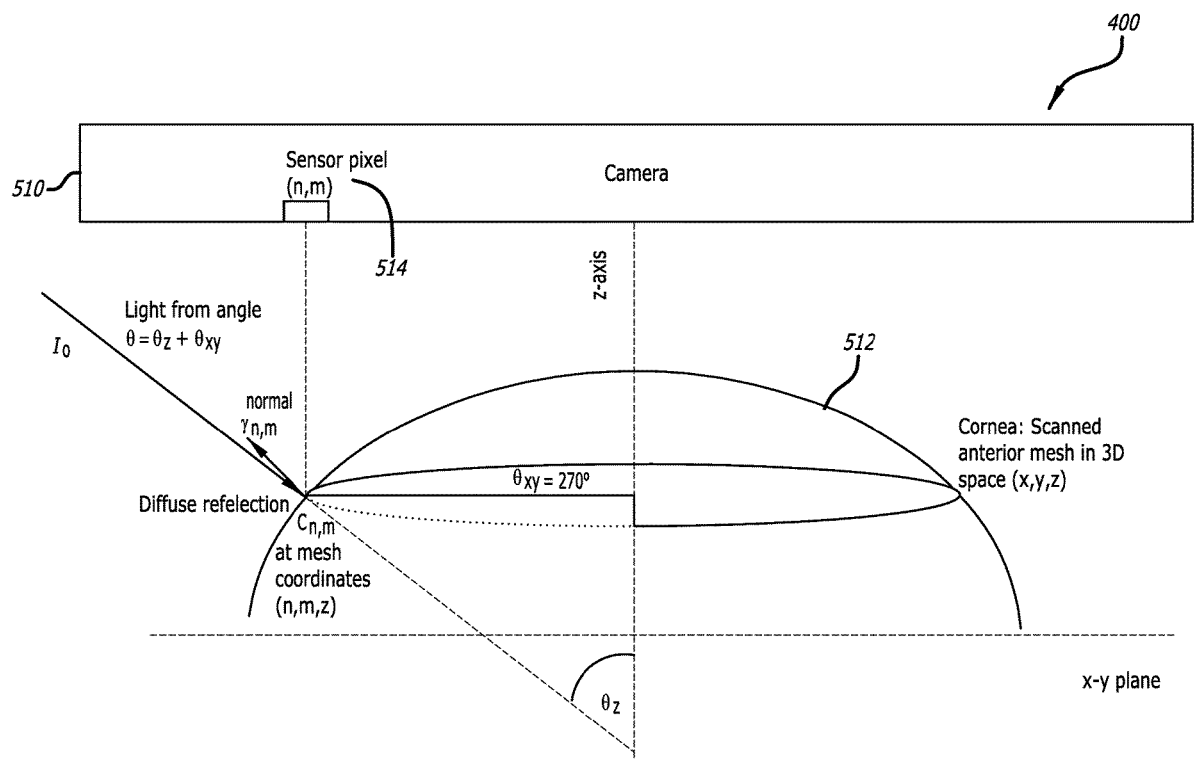
FIGS. 5A-D conceptually illustrates aligning a mesh and an image sequence according to an example aspect of the present disclosure.

FIG. 5A conceptually illustrates an intensity calculation according to an example aspect of the present disclosure. The imaging system 500 includes camera 510 having sensor pixel 514 and an eye 512. The intensity of light captured by sensor pixel 514 is calculated based on light angle $\theta = \theta_z + \theta_{xy}$, initial intensity (e.g. light source) $I_0$, corneal mesh coordinate $c_{n,m}$, and normal vector $\gamma_{n,m}$ as described herein.

As the light moves from the light source, through the eye, and back out through the eye into the imaging device, refraction of the photons in the light occur, particular as the photons move through the different structures within the eye. Before the photons reach the camera sensor, they first pass from the light source through the cornea and aqueous humor to the iris. At this point, the photos can be absorbed, reflected, or scattered. It is in the iris that the events take place that are most significant to determining the (perceived) eye color. The photon's path is refracted several times: 1) at the anterior corneal edge when going from air to corneal stroma, 2) at the posterior corneal edge when going from corneal stroma to aqueous humor, and 3) at the anterior iris' edge, when going from salty tear water of the aqueous humor to the iris' stroma. The light rays (e.g. photons) can be backward-tracked from the camera sensor via the iris to the light sources to calculate the refraction in the sensor pixels of the imaging device.

Figure 5B:
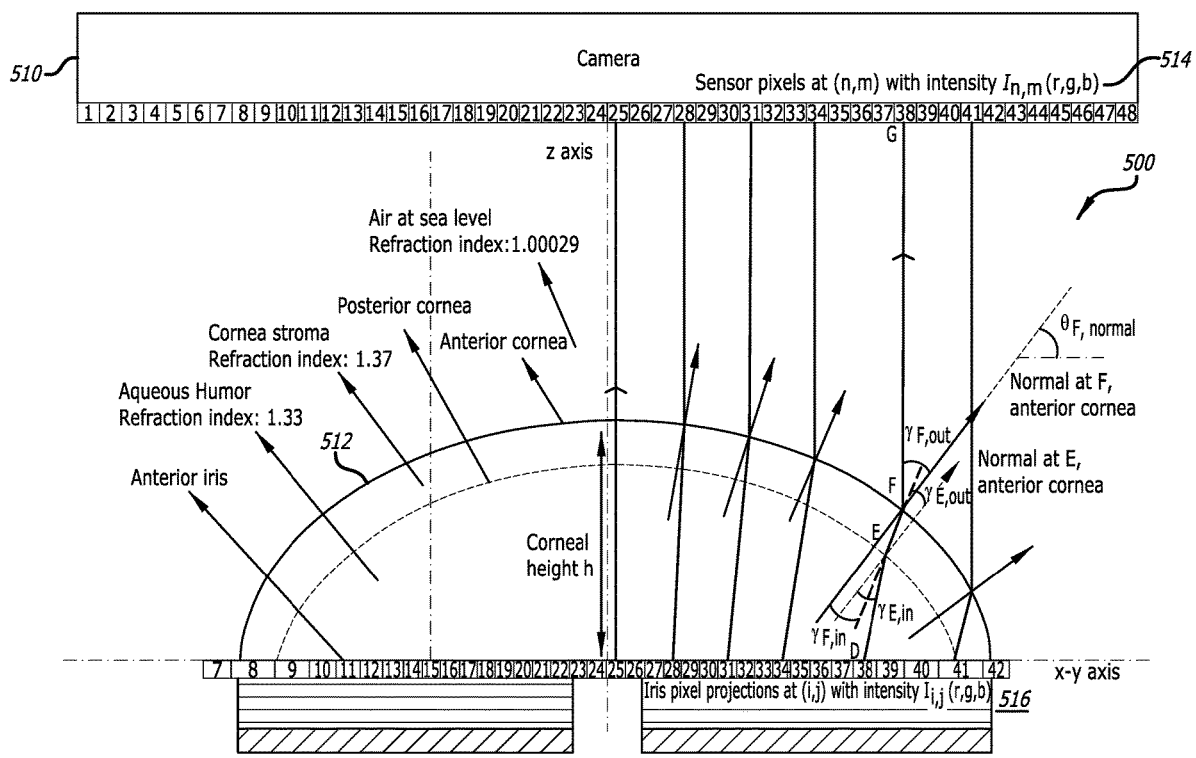

FIG. 5B conceptually illustrates refraction of photons in an imaging system according to an example aspect of the present disclosure. The imaging system 500 includes camera 510 having sensor pixel 514 and an eye 512. Based on the telecentricity of the captured images, the camera sensor pixels receive photons travelling straight towards the sensor (e.g. parallel to the z-axis and the optical axis). When tracing the photons in reverse, starting at the center point of each sensor pixel (n,m), a straight line can be drawn to the anterior edge of the cornea at corneal mesh coordinate $c_{n,m} = (n,m,z)$. Based on F (e.g. the anterior corneal edge) and E (e.g. the posterior corneal edge), the center point of the refracted pixel 516 on the iris (i,j) can be calculated. In several embodiments, the center point of the refracted pixel is calculated using Snell's law. This can be expressed as a refraction projection where (n,m) maps to (i,j). When the images are synchronized, this refraction projection is approximately identical for all images in an image sequence. This simplifies calculations as color calculations for each image can be based on the refracted iris pixels (i,j).

The projection from sensor pixel to iris pixel, (n,m)→(i,j) can be defined based on a line FG, perpendicular to the sensor, where G∈(x,y,z) is center of a sensor pixel (n,m) and F∈(x,y,z) is first intersection of corneal mesh, such that $x_G = x_F = x_n$ and $y_G = x_F = x_m$. Based on this, a photon's exiting angle at F can be calculated. The surface normal at F can be determined based on the capture of the three-dimensional mesh and the image sequence. The angle between surface normal at F and the z-axis can be defined as $\gamma_{F,out}$, which corresponds to the angle that the photon exited out of the cornea on its way to the camera sensor. In a variety of embodiments, $\gamma_{F,out}$ can be expressed as:

$$\gamma_{F,out} = (\text{angle of surface normal at } F \text{ with } z_{axis}) = \frac{\pi}{2} - \theta_{F,normal}$$

If the refractive index n is defined by $$n = \frac{c}{v}$$

where c is the speed of light in vacuum and v is phase velocity of light in the medium, then Snell's Law states that:

$$n_{in} \sin \gamma_{in} = n_{out} \sin \gamma_{out}$$

For point F, where $n_{out} = n_{air}$ (e.g. the refractive index of air) and $n_{in} = n_{cornea}$ (e.g. the refractive index of the cornea), the path through the cornea has angle $\gamma_{F,in}$ with the surface normal at F is:

$$\gamma_{F,in} = \sin^{-1} \frac{n_{out} \sin \gamma_{F,out}}{n_{in}} = \sin^{-1} \frac{1.00029 \sin \gamma_{F,out}}{1.37} = \sin^{-1}(0.73 \sin \gamma_{F,out})$$

In terms of $\theta_{F,normal}$:

$$\gamma_{F,in} = \sin^{-1}(0.73 \sin(\pi/2 - \theta_{F,normal}))$$

or $$\gamma_{F,in} = \sin^{-1}(0.73 \cos \theta_{F,normal})$$

Photons also experience some degree of refraction as they travel through the cornea (e.g. distance EF). The amount of refraction is based on the thickness of the cornea. A typical cornea thickness is approximately 0.6 mm or 600 μm. With this value, the distance of EF in mm can be calculated as follows:

$$EF = \frac{0.6}{\cos \gamma_{F,in}} = \frac{0.6}{\cos(\sin^{-1}(0.73 \sin \gamma_{F,out}))} = \frac{0.6}{\sqrt{1 - (0.73 \sin \gamma_{F,out})^2}}$$

and in terms of $\theta_{F,normal}$:

$$|EF| = \frac{0.6}{\sqrt{1 - (0.73 \cos \theta_{F,normal})^2}}$$

In practice, the cornea is not of uniform thickness. In a variety of embodiments, the thickness of the cornea is between 520 μm and 670 μm. The above calculations can be refined to model the varying thickness by measuring the distance between first and second Purkinje reflections as the Purkinje reflections are related to corneal thickness. In general, the error margin of the refraction through the cornea is:

$$\pm \frac{0.08}{\sqrt{1 - (0.73 \cos \theta_{F,normal})^2}}$$

For point E, where $n_{out} = n_{cornea} = 1.37$ and $n_{in} = n_{aqueous\_humor} = 1.33$, the path through the aqueous humor has angle $\gamma_{E,in}$ with the surface normal at E is:

$$\gamma_{E,in} = \sin^{-1} \frac{n_{out} \sin \gamma_{E,out}}{n_{in}} = \sin^{-1} \frac{1.37 \sin \gamma_{E,out}}{1.33} = \sin^{-1}(1.03 \sin \gamma_{E,out})$$

The normal at F is approximately equal to the normal at E because of the proximity of F and E. Therefore, the angles to the normal of the photon's path can be assumed to be approximately equal:

$$\gamma_{E,out} \approx \gamma_{F,in}$$

and the earlier equation can be expressed in terms of $\gamma_{F,out}$ as follows:

$$\gamma_{E,in} = \sin^{-1}(1.03 \sin \gamma_{E,out}) \approx \sin^{-1}(1.03 \sin \gamma_{F,in}) =$$
$$\sin^{-1}(1.03 \cdot 0.73 \sin \gamma_{F,out}) = \sin^{-1}(0.75 \sin \gamma_{F,out})$$

and in terms of $\theta_{F,normal}$:

$$\gamma_{E,in} = \sin^{-1}(0.75 \cos \theta_{F,normal})$$

The length DE, the path through the aqueous humor, can be calculated based on the height of the cornea $h_c$ and the distance from cornea to the lens. In a variety of embodiments, $h_c = 3.4$ mm can be used as a constant value. However, the corneal height is typically around 4.2 mm in young people and as low as 2.4 mm in older people. In several embodiments, $h_c$ can be calculated based on the distance between the first (anterior cornea) and third (lens) Purkinje reflections.

With angle $\gamma_{E,in}$, a line from point E angled in direction $\gamma_{E,in}$ can be established, with point D defined as the intersection of this line with the iris plane. Point $D \in (x,y,z)$, the center point of pixel (i,j), is defined as:

$$\cos(\gamma_{F,out} - \gamma_{E,in}) = \frac{z_E}{DE}$$

and $$DE = \frac{z_E}{\cos\left(\frac{\pi}{2} - \theta_{F,normal} - \sin^{-1}(0.75 \cos \theta_{F,normal})\right)}$$

As $$\cos(\sin^{-1}(0.75 \cos(\theta))) = \sqrt{(1 + 0.75 \cos \theta_{F,normal})(1 - 0.75 \cos \theta_{F,normal})}$$

and $$\cos(\alpha - \beta) = \cos \alpha \cos \beta + \sin \alpha \sin \beta$$

then $$|DE| = \frac{z_E}{0.75 \cos^2 \theta_{F,normal} + \sin \theta_{F,normal} \sqrt{(1 + 0.75 \cos \theta_{F,normal})(1 - 0.75 \cos \theta_{F,normal})}}$$

Figure 5C:
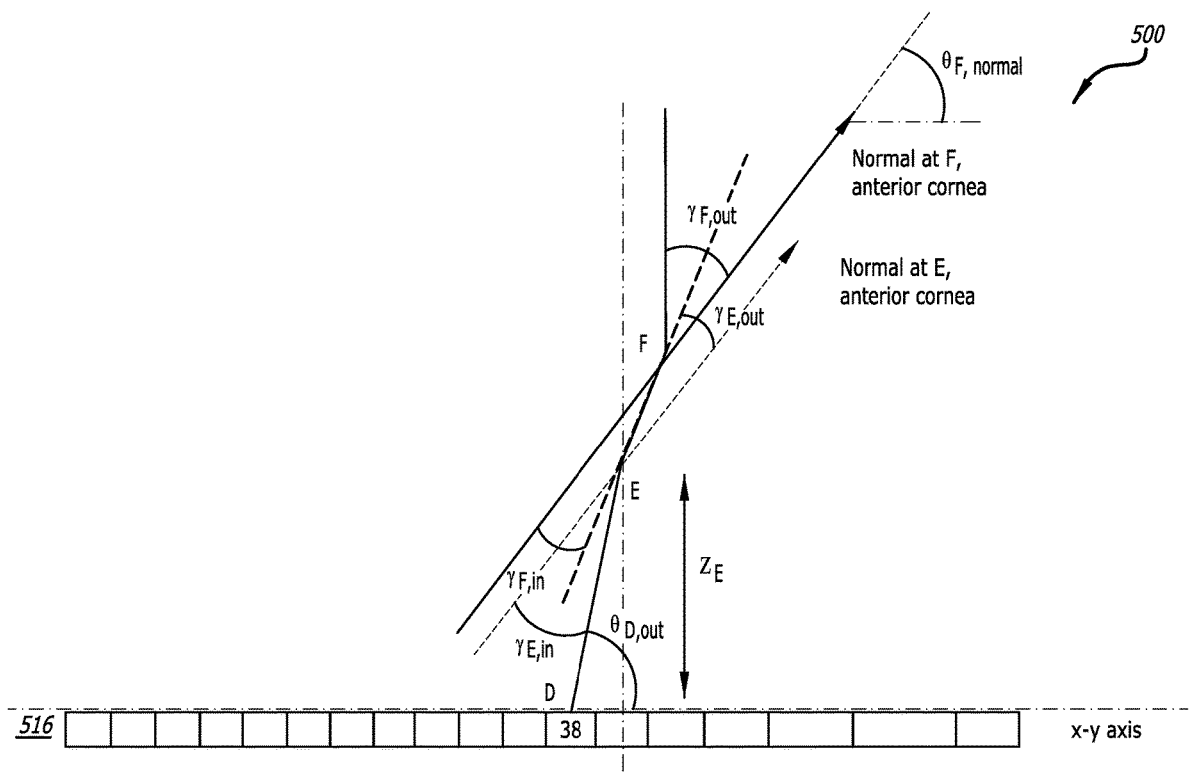

FIG. 5C conceptually illustrates a summary of coordinates within in an imaging system 500 with reference to iris pixels 516 according to an example aspect of the present disclosure. For point F, if F(x,y,z) and normal at F, $\theta_{F,normal}$ is known, then, for point E, the angle of vector EF can be expressed as:

$$\theta_{\overrightarrow{EF}} = \theta_{F,normal} - \gamma_{F,in} = \theta_{F,normal} - \sin^{-1}(0.73 \cos \theta_{F,normal})$$

and the length EF as:

$$|EF| = \frac{0.6}{\sqrt{1 - (0.73 \cos \theta_{F,normal})^2}}$$

For point D, the angle of vector DE can be expressed as:

$$\theta_{\overrightarrow{DE}} = \theta_{E,normal} - \gamma_{E,in} \approx \theta_{F,normal} - \sin^{-1}(0.75 \cos \theta_{F,normal})$$

and length DE as:

$$|DE| = \frac{z_E}{0.75 \cos^2 \theta_{F,normal} + \sin \theta_{F,normal} \sqrt{(1 + 0.75 \cos \theta_{F,normal})(1 - 0.75 \cos \theta_{F,normal})}}$$

With D, the midpoint of pixel (i,j) and E, the intersection at posterior surface of the cornea, as well as the refraction angles at anterior and posterior surface of the cornea are defined for the image sequence, the refracted photon paths of the different lights coming into pixel midpoints of (i,j) can be calculated.

Figure 5D:
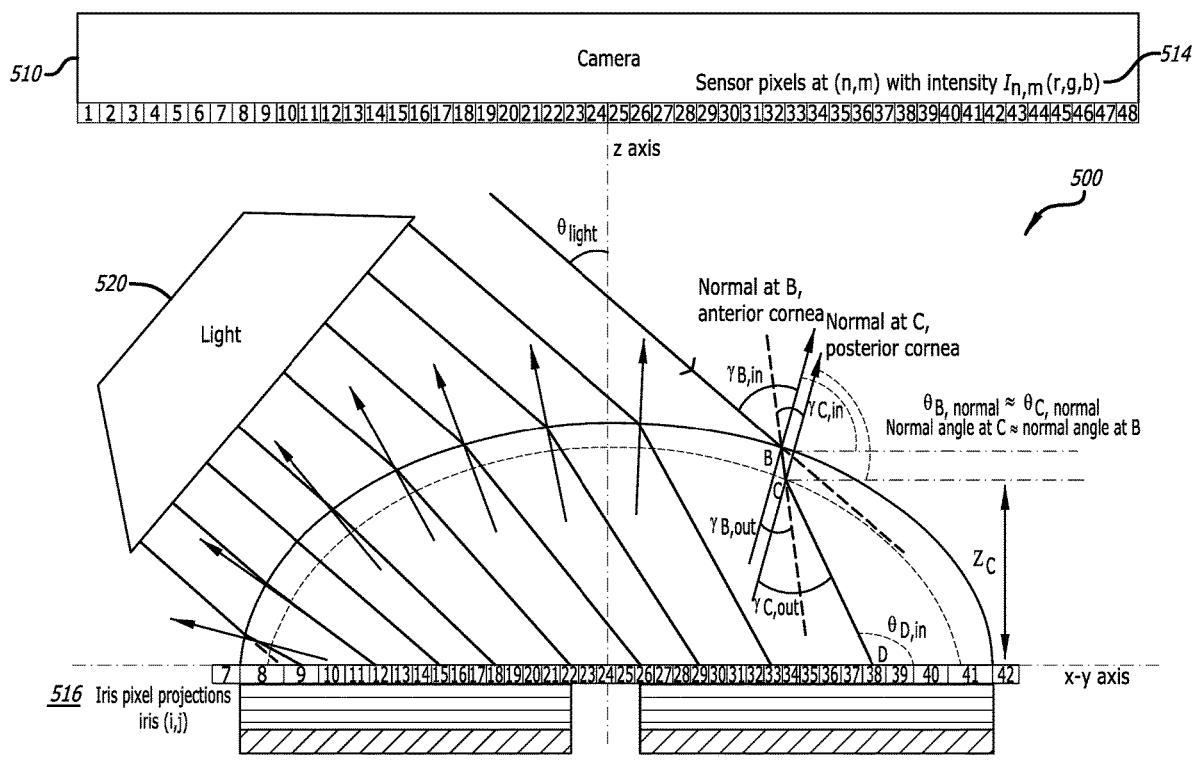

The refraction of photons' paths from the light sources to the iris can be calculated, in particular the intensity $I_{i,j}(r,g,b)$ of a photon travelling from a light source to iris pixel (i,j), with angle of the light $\theta_{light}$. In several embodiments, the intensity can be back-calculated from mid-point of iris pixel (i,j) to the light source. In a number of embodiments, this calculation can be based on Snell's Law. Turning now to FIG. 5D, a conceptual illustration of an intensity calculation from a light source 520 within in an imaging system 500 according to an example aspect of the present disclosure is shown. In many embodiments, the normal at B, the anterior corneal surface, is approximately equal to the normal at C, the posterior corneal surface and therefore $\gamma_{C,in} = \gamma_{B,out}$ Based on $\theta_{light}$ and $\theta_{B,normal}$ $$\gamma_{B,in} = \theta_{light} + \left(\frac{\pi}{2} - \theta_{B,normal}\right)$$

$$\gamma_{C,out} = \sin^{-1}(0.75 \cos \theta_{B,normal})$$

$$\gamma_{B,out} = \sin^{-1}(0.73 \cos \theta_{B,normal})$$

Lengths CD and BC can be calculated as:

$$|CD| = \frac{z_c}{0.75 \cos^2 \theta_{B,normal} + \sin \theta_{B,normal} \sqrt{(1 + 0.75 \cos \theta_{B,normal})(1 - 0.75 \cos \theta_{B,normal})}}$$

$$|BC| = \frac{0.6}{\sqrt{1 - (0.73 \cos \theta_{B,normal})^2}}$$

Iris Specular and Ambient Occlusion Separation

As described herein, image synchronization (e.g. image matching) can be based on cornea measurements and subsequent refraction calculations through reverse ray-tracing of each camera sensor pixel's center point from the camera through the cornea to the iris and then from the iris through the cornea to each light source. These image synchronization techniques allow for a variety of additional modeling including, but not limited to, iris ambient occlusion calculation, melanin absorption coefficient calculation, and iris stroma' scatter coefficient calculations.

The strongest specular reflections of the eye are typically the three Purkinje reflections that reflect off the corneal anterior surface, off the corneal interior surface and off the lens. However, these reflections are typically not useful for determining eye models in accordance with embodiments of the invention. In a variety of embodiments, the specular reflection directly off the anterior edge off the iris is used in the generation of eye models. In several embodiments, the iris at a smooth surface; however, due to the unordered collagen fibril stroma of the iris, the surface of the iris is typically not smooth. The uneven surface of the iris causes brighter pixels where the light reflects directly off the fibers into the camera, such as via the $\theta_{out}$ angle. This can also cause certain pixels to be darker where higher-positioned fibers shade occluded fibers. In order to address these issues, the specular reflection and/or the occlusion shadows can be separated from the other optical phenomena, such as absorption and scattering.

Typically, specular reflection and shading are mostly independent of wavelength of light, whereas absorption and scattering in the iris is mostly dependent on the wavelength of light. In addition, the contrast between occlusion shadow and specular reflection will be significantly lower on the coaxially lit image, where $\theta_z=0$ compared to the side lit images where $|\theta_z|>0$.

In many embodiments, pheomelanin colors can be represented in RGB, with r=255, 100<g<200, and b=0. This correlates to wavelengths $\lambda$ between 600 and 625 nm. Accordingly, pheomelanin can be represented in RGB as $(r,g,b) \in [(2.55 \cdot g, g, 0), (1.28 \cdot g, g, 0)]$. In several embodiments, eumelanin colors can be represented in RGB, with 200<r<255, g=0, and b=0. This correlates to wavelengths $\lambda$ between 700 and 780 nm. Accordingly, eumelanin can be represented in RGB as $(r,g,b) \in [(r,0,0), (r,0,0)]$.

In a variety of embodiments, scattering in the iris' stroma is inversely proportional to the fourth power of the wavelength (nm). When the source light is white, i.e. $(r,g,b)=(c,c,c)$ for a constant c E [0,255]:

$$\text{if } 100\% \text{ Blue: } (0,0,255) \equiv 440\text{nm then } I_{scatter,blue} \sim \frac{1}{\lambda_b^4} = 2.67 \cdot 10^{25}$$

$$\text{if } 100\% \text{ Green: } (0,255,0) \equiv 510\text{nm then } \frac{I_{scatter,green}}{I_{scatter,blue}} \sim \frac{\lambda_b^4}{\lambda_g^4} = 0.554$$

$$\text{if } 100\% \text{ Red: } (255,0,0) \equiv 600\text{nm then } \frac{I_{scatter,red}}{I_{scatter,blue}} \sim \frac{\lambda_b^4}{\lambda_r^4} = 0.289$$

In several embodiments, maximum scatter is $(r,g,b)=(0.289 \cdot 255, 0.554 \cdot 255, 255)=(74,141,255)$. In a number of embodiments, minimum scatter is $(r,g,b)=(1.156, 2.216, 4) \approx (1,2,4)$. More generally, for scattering:

$$\text{if } b=x \Rightarrow (r,g,b)=(0.289 \cdot x, 0.554 \cdot x, x)$$

In many embodiments, the following steps can be taken to separate specular from melanin absorption and scattering. To determine separate scattering for intensity pixel matrix $I_{i,j}(r,g,b) \in (\mathbb{N}, \mathbb{N}, \mathbb{N})$, split off scatter as follows:

$$I'_{i,j}(r) = I_{i,j}(r) - 0.289 \cdot s_{i,j}$$
$$I'_{i,j}(g) = I_{i,j}(g) - 0.554 \cdot s_{i,j}$$
$$I'_{i,j}(b) = I_{i,j}(b) - s_{i,j}$$
$$\text{where } \max_{I'_{i,j}(r,g,b) \geq (0,0,0)} (s_{i,j})$$

A scatter map matrix can be defined as:

$$S_{i,j}(r,g,b) = (0.289 \cdot s_{i,j}, 0.554 \cdot s_{i,j}, s_{i,j})$$

Separate specular and ambient occlusion can be calculated. For intensity pixel matrix $I'_{i,j}(r,g,b) \in (\mathbb{N}, \mathbb{N}, \mathbb{N})$, specular and ambient occlusion can be separated as follows:

$$I''_{i,j}(r) = I'_{i,j}(r) - a_{i,j}$$
$$I''_{i,j}(g) = I'_{i,j}(g) - a_{i,j}$$
$$I''_{i,j}(b) = I'_{i,j}(b) - a_{i,j}$$
$$\text{where } \max_{I''_{i,j}(r,g,b) \geq (0,0,0)} (a_{i,j})$$

A specular and ambient occlusion map matrix can be defined as:

$$A_{i,j}(r,g,b) = (a_{i,j}, a_{i,j}, a_{i,j})$$

After separating scattering, specular and ambient occlusion, the remaining structures left to model in the eye are mostly melanin, which includes either or both of eumelanin and pheomelanin. As described herein, neither the eumelanin nor pheomelanin have blue—pheomelanin has both green and red in it, whereas eumelanin only has red. Based on this observation, for intensity pixel matrix $I''_{i,j}(r,g,b) \in (\mathbb{N}, \mathbb{N}, \mathbb{N})$, the pheomelanin can be split off as follows:

$$I'''_{i,j}(r) = I''_{i,j}(r) - t \cdot p_{i,j}$$
$$I'''_{i,j}(g) = I''_{i,j}(g) - p_{i,j}$$
$$I'''_{i,j}(b) = I''_{i,j}(b)$$
$$\text{where } 1.28 \leq t \leq 2.55 \text{ and } \max_{I'''_{i,j}(r,g,b) \geq (0,0,0)} (p_{i,j}).$$

Then the pheomelanin map matrix can be defined as:

$$P_{i,j}(r,g,b) = (t \cdot p_{i,j}, p_{i,j}, 0)$$

and the eumelanin map matrix can be defined as:

$$E_{i,j}(r,g,b) = I'''_{i,j}(r,g,b)$$

As described above, the primary objective is to split off specular and ambient occlusion in order to more accurately model the iris. In several embodiments, the above-described techniques model the complex light effects on the iris as linear functions in the (r,g,b) space. It is of course more complex than this. In order to complete the splitting of the specular and ambient occlusions, we can split $A_{i,j}(r,g,b)$ from the intensity matrix as follows:

$$I_{i,j}(r,g,b) = E_{i,j}(r,g,b) + P_{i,j}(r,g,b) + S_{i,j}(r,g,b)$$

Figure 6:
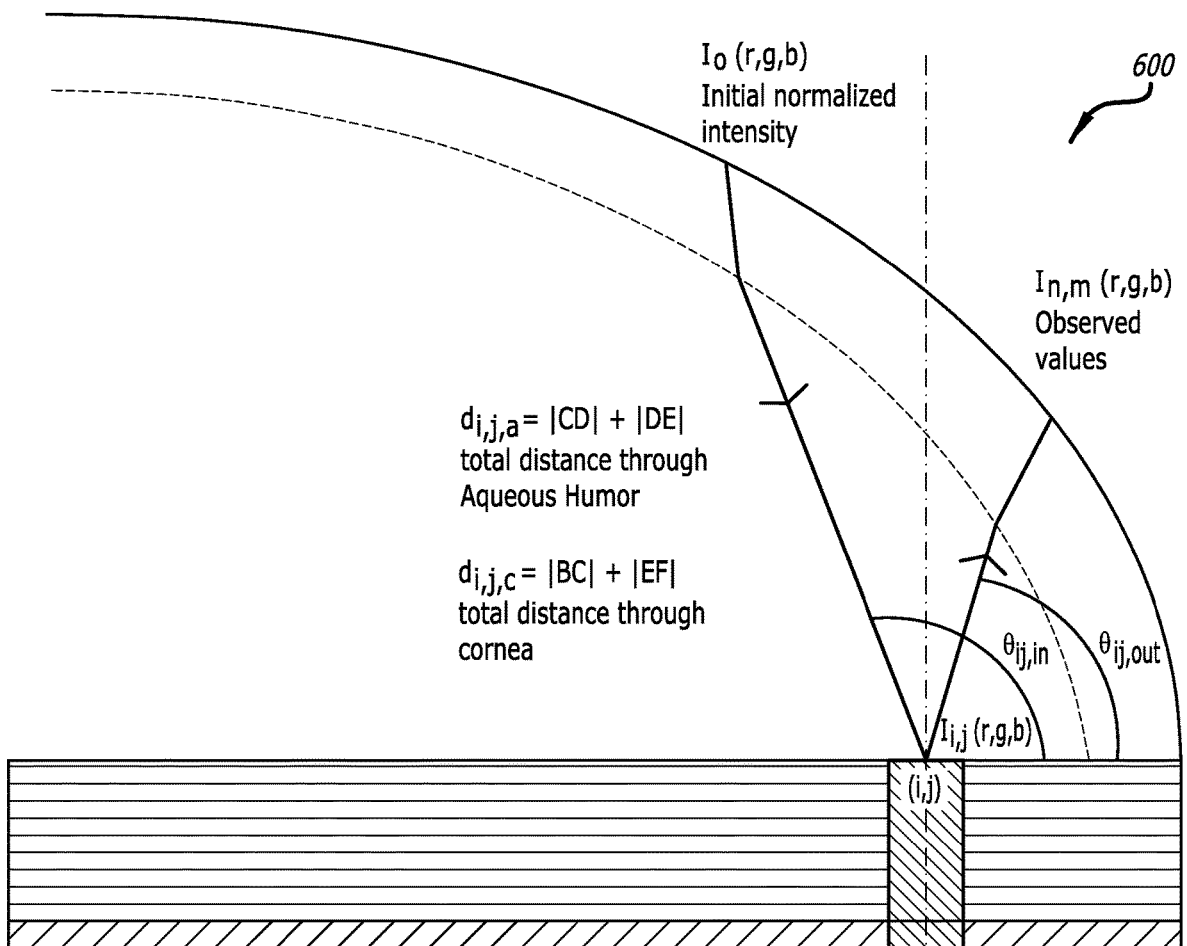
FIG. 6 conceptually illustrates scattering and absorption calculations according to an example aspect of the present disclosure.

The intensity due to scattering and absorption can be separated in a second pass. For simplicity, this process will be described in accordance with a single pixel 610 (i,j) as shown in FIG. 6. However, the calculations are typically performed on some or all of the pixels as described herein. FIG. 6 conceptually illustrates scattering and absorption calculations according to an example aspect of the present disclosure.

The incident and outgoing angle at each pixel 610 (i,j) can be calculated as described herein. Similarly, the initial intensity, $I_0(r,g,b)$, the distance travelled through aqueous humor, $d_{ij,a}$, and the distance travelled through cornea, $d_{ij,c}$, for each pixel (i,j) have been calculated as described herein. In many embodiments, the initial intensity can include intensity loss due to travel through air before reaching the cornea. Additionally, the observed intensity at the imaging sensor, $I_{n,m}(r,g,b)$ can be measured at the time the image(s) in the image sequence are captured. In many embodiments, when the image sequence includes five images as described herein:

$$I_{i,j} \rightarrow \begin{bmatrix} r(0, \theta_{in}, \theta_{out}, I_0, I_{n,m}, d_a, d_c) & g(0, \theta_{in}, \theta_{out}, I_0, I_{n,m}, d_a, d_c) & b(0, \theta_{in}, \theta_{out}, I_0, I_{n,m}, d_a, d_c) \\ r(0, \theta_{in}, \theta_{out}, I_0, I_{n,m}, d_a, d_c) & g(0, \theta_{in}, \theta_{out}, I_0, I_{n,m}, d_a, d_c) & b(0, \theta_{in}, \theta_{out}, I_0, I_{n,m}, d_a, d_c) \\ r(90, \theta_{in}, \theta_{out}, I_0, I_{n,m}, d_a, d_c) & g(90, \theta_{in}, \theta_{out}, I_0, I_{n,m}, d_a, d_c) & b(90, \theta_{in}, \theta_{out}, I_0, I_{n,m}, d_a, d_c) \\ r(180, \theta_{in}, \theta_{out}, I_0, I_{n,m}, d_a, d_c) & g(180, \theta_{in}, \theta_{out}, I_0, I_{n,m}, d_a, d_c) & b(180, \theta_{in}, \theta_{out}, I_0, I_{n,m}, d_a, d_c) \\ r(270, \theta_{in}, \theta_{out}, I_0, I_{n,m}, d_a, d_c) & g(270, \theta_{in}, \theta_{out}, I_0, I_{n,m}, d_a, d_c) & b(270, \theta_{in}, \theta_{out}, I_0, I_{n,m}, d_a, d_c) \end{bmatrix} \equiv$$

$$\begin{bmatrix} \text{coaxial} \\ \text{left}|OD \text{ nasal}|OS \text{ temp} \\ \text{right}|OD \text{ temp}|OS \text{ nasal} \\ \text{above} \\ \text{below} \end{bmatrix}$$

The scatter intensity model $I_{n,m}(r,g,b)$ can be defined as:

$$I_{n,m}(r,g,b) = E_{n,m}(r,g,b) + P_{n,m}(r,g,b) + S_{n,m}(r,g,b)$$

where $E_{n,m}(r,g,b)$ is the eumelanin reflection intensity in $\theta_{ij,out}$ direction, $P_{n,m}(r,g,b)$ is the pheomelanin reflection intensity in $\theta_{ij,out}$ direction, and $S_{n,m}(r,g,b)$ is the Mie scattering intensity in $\theta_{ij,out}$ direction.

The absorption coefficient $\mu_a[\text{cm}^{-1}]$ of melanosomes can differ significantly depending on the density of the melanosomes. The general shape of the melanosome absorption spectrum can be approximated as:

$$\mu_a \sim \frac{1}{\lambda^{3.48}}$$

where $\lambda$ [nm] is the wavelength of the incident light.

In a variety of embodiments, $\mu_a = 1.70 \cdot 10^{12} \cdot \lambda^{-3.48}$ for melanosomes in skin, while $\mu_a = 6.49 \cdot 10^{12} \cdot \lambda^{-3.48}$ for melanosomes in the retina. Melanosomes in the iris can be approximated as:

$$\mu_a = M' \cdot \lambda^{-3.48} \text{ with } 1.70 \cdot 10^{12} < M' < 6.49 \cdot 10^{12}$$

In several embodiments, the likelihood that melanin will reflect is given by Beer's law:

$$R_m = 1 - e^{-\mu_{a,m} d_m},$$

where $\mu_{a,m}$ is the absorption coefficient of melanin and $d_m$ is the thickness of the melanin layer. In a variety of embodiments:

$$5 \text{ μm} < d_m < 10 \text{ μm}$$

Eumelanin and pheomelanin reflections at (n,m) can occur in direction $\theta_{ij,out}$:

$$E_{n,m}(r,g,b) + P_{n,m}(r,g,b) = I_0(r,g,b) \cdot (T_{cornea} + T_{aq \cdot humor}) \cdot (1 - e^{-\mu_{a,m} d_m}) \cdot f(\theta_{ij,out})$$

where f is the coefficient of diffuse reflection in the $\theta_{ij,out}$ direction.

Light is subject to absorption when traveling through the cornea and aqueous humor. The photon survival rate T can be given by Beer's law:

$$T_{aq \cdot humor} = T(d_{ij,aq}) = e^{-\mu_{a,aq} d_{ij,a}}$$

where $\mu_{a,a}$ is the absorption coefficient of water and $$T_{cornea} = T(d_{ij,c}) = e^{-\mu_{a,c} d_{ij,c}}$$

where $\mu_{a,c}$ is the absorption coefficient of the cornea.

In several embodiments, $T_{cornea}$ is constant and $T_{aq \cdot humor}$ is a linear function of distance travelled in the aqueous humor, $d_{ij,a}$.

The melanin can be modeled as a top layer filter through which the photon travels before reaching the stroma of the iris. Some of these photons will interact by the melanin filter depending on how much melanin there is. The survival rate of the photons traveling through melanin can also be given by Beer's law:

$$T_{melanin} = T_m = e^{-\mu_{a,m} d_m}$$

where $\mu_{am}$ is absorption coefficient of melanin and $d_m$ is the thickness of the melanin layer. In a variety of embodiments:

$$5 \text{ μm} < d_m < 10 \text{ μm}$$

as described herein.

Mie scattering describes the scattering of an electromagnetic plane wave by a homogeneous sphere. In a variety of embodiments, the eye is approximately modeled as a homogeneous sphere. In several embodiments, the scattering of the photons $S_{n,m}(r,g,b)$ can be expressed as:

$$S_{n,m}(r,g,b) = I_0(r,g,b) \cdot (e^{-\mu_{a,c} d_{ij,c}} + e^{-\mu_{a,aq} d_{ij,a}} + e^{-\mu_{a,m} d_m}) \beta(\lambda) \cdot \gamma(\theta)$$

where $\beta(\lambda)$ is the Mie scattering coefficient and $\gamma(\theta)$ is the scattering phase function. In many embodiments, $\beta(\lambda)$ can be approximated as:

$$\beta(\lambda) = \frac{8\pi^3 (n^2 - 1)^2}{3} \cdot \frac{1}{N} \cdot \frac{1}{\lambda^4}$$

where n is the refractive index of iris' stroma and N is the molecular number density of the iris' stroma.

In a number of embodiments, γ(θ) can be approximated as:

$$\gamma(\theta) = \frac{1}{4\pi} \cdot \frac{1-g^2}{\left(1+g^2 - 2g\cos\theta_{ij,out}\right)^{3/2}}$$

where g is the anisotropy of the scattering, which indicates the direction and shape of the scattering.

If the refractive index of iris equals that of the cornea, n=1.37, then:

$$S_{n,m}(r, g, b) = I_0(r, g, b) \cdot$$

$$\left(e^{-\mu_{a,c}d_{ij,c}} + e^{-\mu_{a,aq}d_{ij,a}} + e^{-\mu_{a,m}d_m}\right) \cdot \frac{5}{N} \cdot \frac{1}{\lambda^4} \cdot \frac{1-g^2}{\left(1+g^2 - 2g\cos\theta\right)^{3/2}}$$

In many embodiments, the scatter density N and anisotropy g, as well as absorption coefficient $\mu_{a,m}$ of melanin for each pixel (i,j) can be calculated. These values can be used to define the optical properties of the image sequence.

Figure 7:
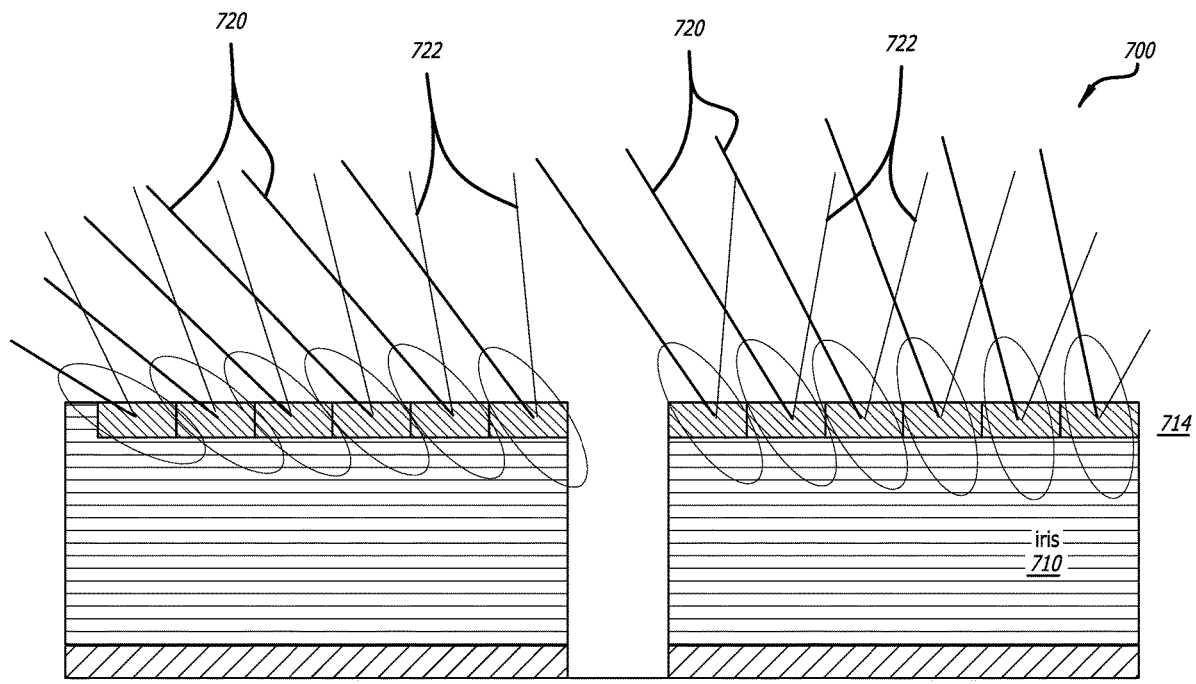
FIG. 7 conceptually illustrates iris top surface scattering according to an example aspect of the present disclosure.

A variety of scatter models can be used to model the scattering of light off the iris. FIG. 7 conceptually illustrates iris top surface scattering according to an example aspect of the present disclosure. In the scatter model 700, the iris stroma 710 is modeled as having no depth. The scatter intensity of each pixel 714 (i,j) can be calculated separately as shown in FIG. 7. The lines 720 represent the incident photons and lines 722 indicate the scattering effect in the direction that is observed by the imaging device. In this model, each pixel 714 can be described based on a singular path of a photon.

Figure 8A:
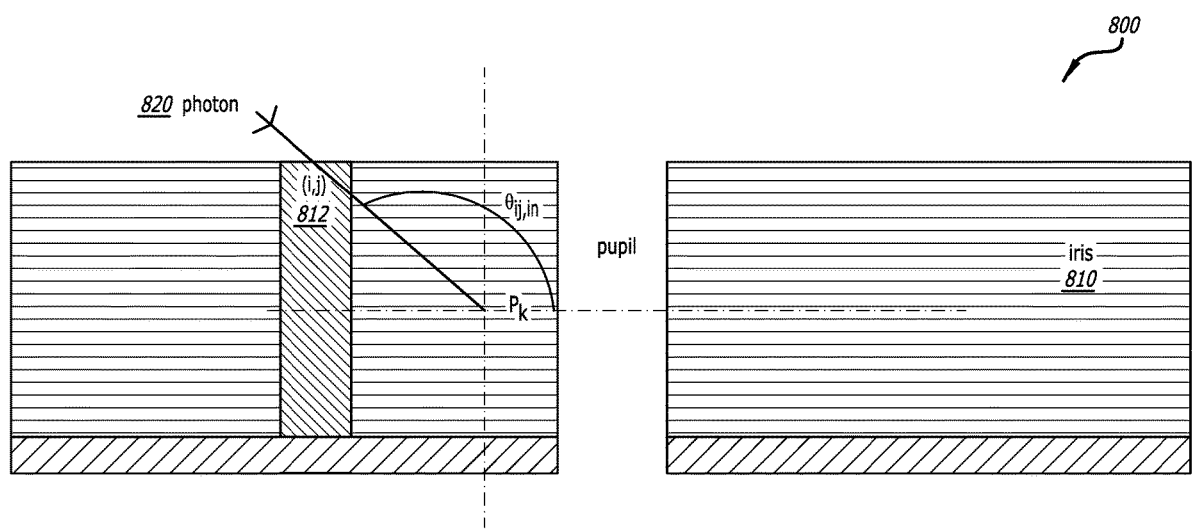
FIGS. 8A-C conceptually illustrates iris subsurface scattering according to an example aspect of the present disclosure.
Figure 8B:
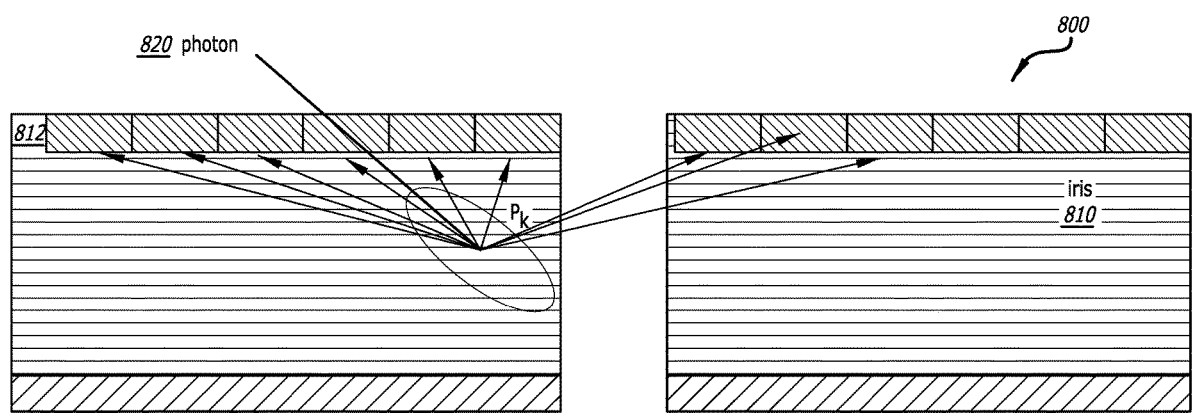
Figure 8C:
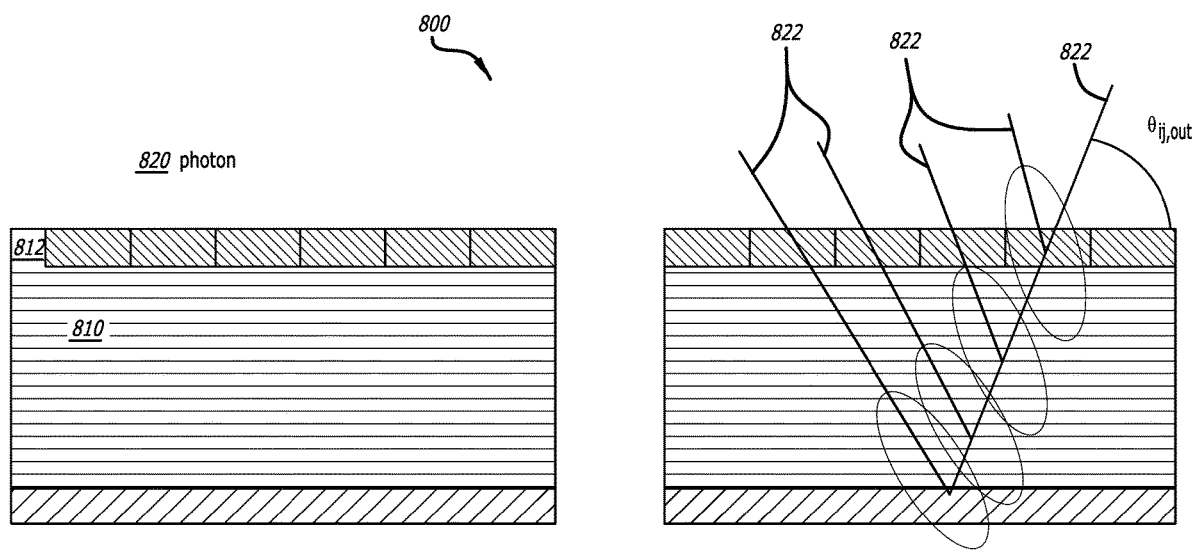

FIGS. 8A-C conceptually illustrates iris subsurface scattering according to an example aspect of the present disclosure. In the scatter model 800, the iris is modeled as having depth of approximately 600 microns as described herein. Turning now to FIG. 8A, scatter model 800 includes a photon 820 traveling in a straight line through pixel 812 (i,j) in direction $\theta_{ij,in}$ before it scatters somewhere inside the iris depth 810 as described herein. In several embodiments, the photon 820 scatters in all directions towards the other iris pixels 812 as shown in FIG. 8B. However, the imaging device observes those scatters that escape the iris pixels 812 in direction $\theta_{out}$. All the scattering received by the iris pixels 812 will be summed up to derive the final intensity due to scattering. In many embodiments, the scattering can be calculated by back-calculating the photon path from the imaging device as described herein. As shown in FIG. 8C, the outgoing photon path 822 can be observed by the camera. The scatter intensity of pixel 812 (i,j) can be calculated as the sum of scatter points where the outgoing path 812 intersects with incoming photon paths 824 of the other iris pixels as described herein.

Figure 9:
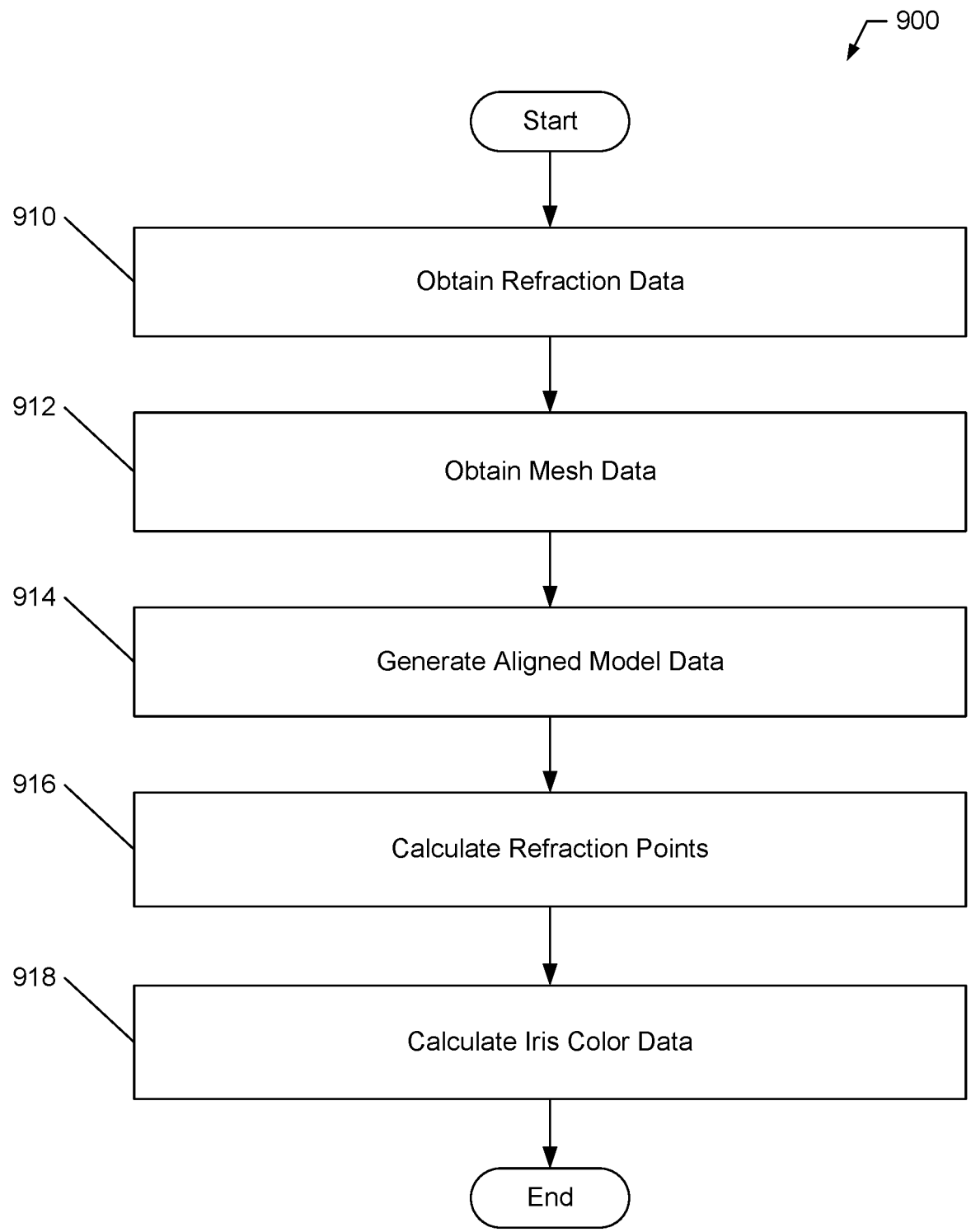
FIG. 9 illustrates a flowchart of a process for generating eye models with accurate iris colors in an example aspect of the present disclosure.

FIG. 9 illustrates a flowchart of a process 900 for generating eye models with accurate iris colors in an example aspect of the present disclosure. Refraction data can be obtained (910). In a variety of embodiments, the refraction data includes an image sequence captured using an imaging device coaxially located to an eye as described herein. Mesh data can be obtained (912). In many embodiments, the mesh data can be obtained using an imaging device that captures the anterior surface of the eye as described herein. Aligned model data can be generated (914). In a number of embodiments, the aligned model data is generated by aligning the refraction data and the mesh data based on the coaxial alignment of the imaging devices relative to the eye as described herein. Refraction points in the aligned model data can be calculated (916). In several embodiments, the refraction points are calculated in and between various structures of the eye as described herein. Iris color data can be calculated (918). In a variety of embodiments, the iris color data is calculated based on the refraction points and the aligned model data by calculating melanin information for the aligned model data based on the refraction points for iris pixels in the aligned model data. In this way, the iris color data can indicate the color of light reflected by the iris as calculated based on the light transmitted by a light source into the eye and reflected by the various structures of the eye back out to the imaging device as described herein. A variety of techniques that can be used to model an iris color that can be used in accordance with embodiments of the invention are described in more detail with respect to FIG. 11.

Although the process 900 is described with reference to the flowchart illustrated in FIG. 9, it will be appreciated that many other methods of performing the acts associated with the process 900 may be used. For example, the order of some of the blocks may be changed, certain blocks may be combined with other blocks, one or more blocks may be repeated, and some of the blocks described are optional. The process 900 may be performed by processing logic that may include hardware (circuitry, dedicated logic, etc.), software, or a combination of both.

Once generated, the eye models herein can be integrated into a variety of computer-generated models. For example, the eye models can be used to provide accurate, realistic eyes for computer gaming, virtual environments, and/or any other computer-generated models.

Figure 10:
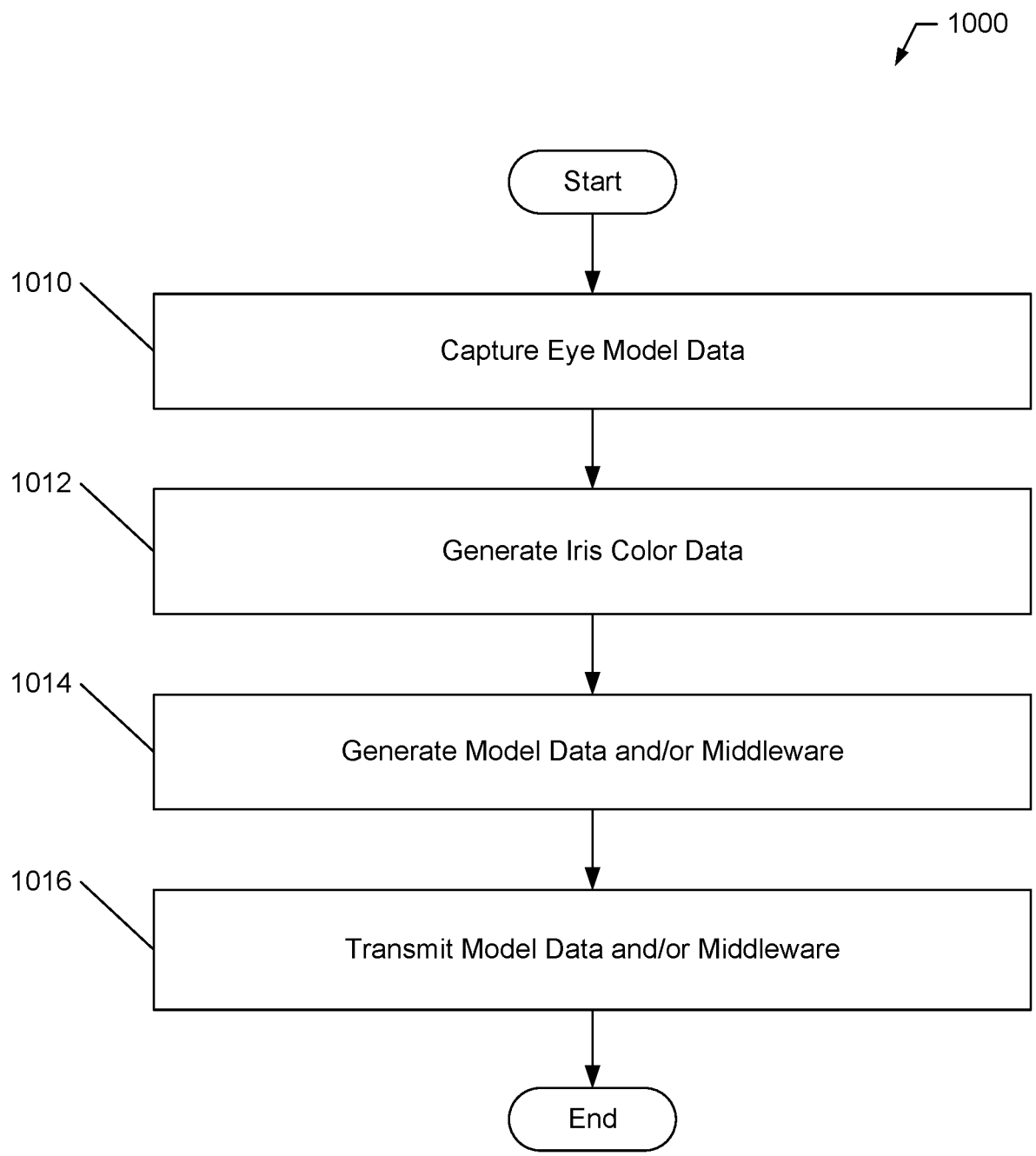
FIG. 10 illustrates a flowchart of a process for providing eye models with accurate iris colors in an example aspect of the present disclosure.

FIG. 10 illustrates a flowchart of a process 1000 for providing eye models with accurate iris colors in an example aspect of the present disclosure. Eye model data can be captured (1010). In many embodiments, the eye model data includes an image sequence including refraction data from various angles of an eye and a three-dimensional mesh of the surface of the eye as described herein. Iris color data can be generated (1012). In a variety of embodiments, the iris color data is an accurate representation of the color of the iris of the eye calculated based on the eye model data as described herein. Model data and/or middleware can be generated (1014). In several embodiments, the model data includes one or more computer-generated models of the structure of the eye and the iris color data such that the model data is an accurate model of the captured eye(s) as described herein. In a number of embodiments, the model data can be manipulated within a computer-generated environment to accurately represent the eyes from a variety of perspectives other than those captured during the modeling process as described herein. In many embodiments, middleware can include instructions that can be used to accurately generate eyes having accurate shapes, iris colors, and movement in computer generated models provided by a third party. For example, the middleware can be used by a game developer to add realistic eyes to a computer-generated avatar in a virtual environment without capturing the eye model data and/or iris color data as described herein. The model data and/or middleware can be transmitted (1016). The model data and/or middleware can be transmitted to a variety of systems for visualization and/or incorporation into other computer-generated models and/or virtual environments as described herein.

Although the process 1000 is described with reference to the flowchart illustrated in FIG. 10, it will be appreciated that many other methods of performing the acts associated with the process 1000 may be used. For example, the order of some of the blocks may be changed, certain blocks may be combined with other blocks, one or more blocks may be repeated, and some of the blocks described are optional. The process 1000 may be performed by processing logic that may include hardware (circuitry, dedicated logic, etc.), software, or a combination of both.

As described herein, the concentration of melanin pigmentation in the iris can be used to determine the structural color of the iris under different lighting environments. In a variety of embodiments, the following variables are used to determine melanin concentration:

eumelanin concentration (mg/ml): $c_{eu}(i,j)$
pheomelanin concentration (mg/ml): $c_{pheo}(i,j)$
ratio of melanin in the ABL versus total melanin in iris: $r_A(i,j)$ where (i,j) is a pixel (or pixel set), and where the anterior base layer (ABL) and the stroma are 2 layers of the iris.

Figure 11:
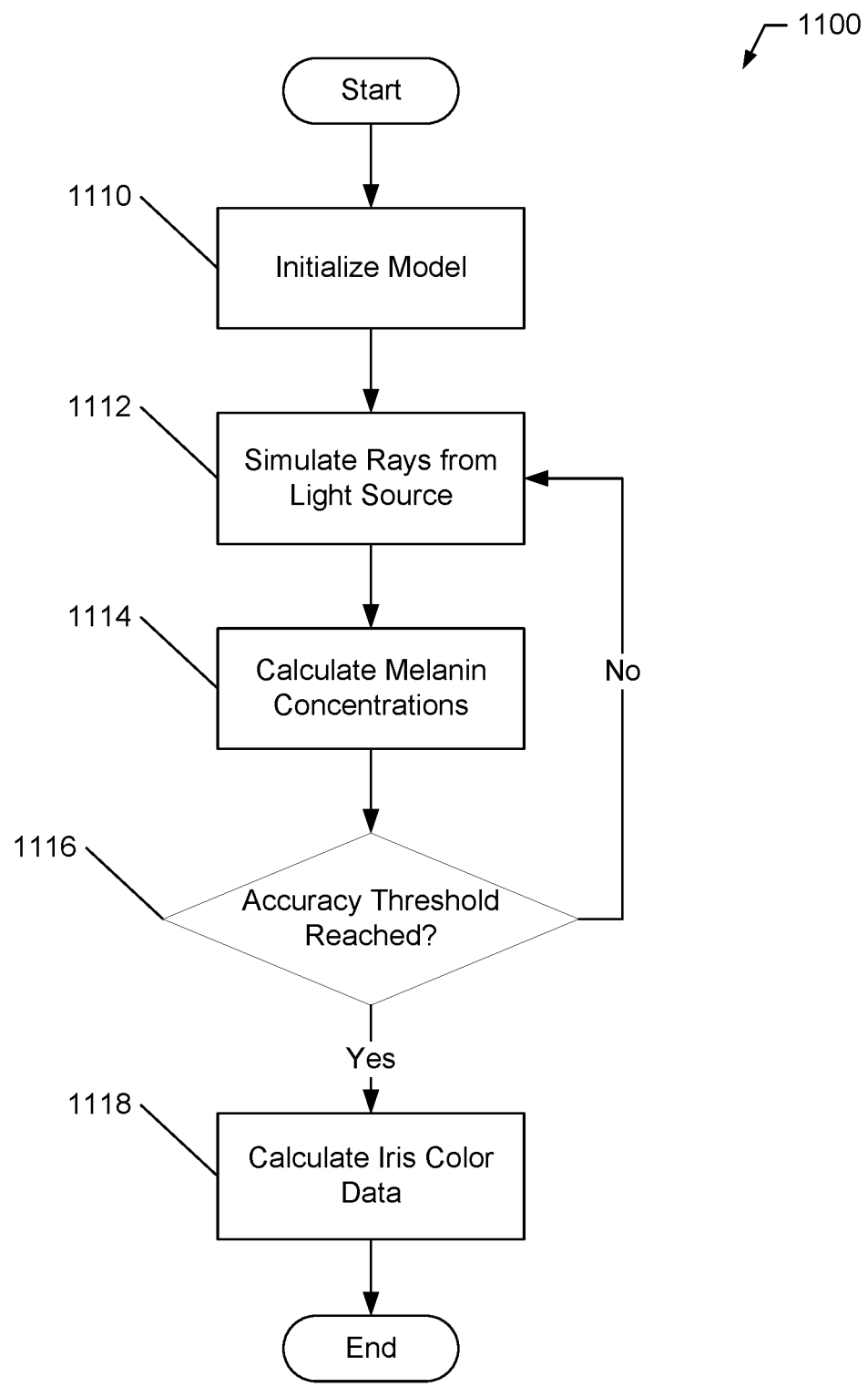
FIG. 11 illustrates a flowchart of a process for simulating the structural color of the iris in an example aspect of the present disclosure.

FIG. 11 illustrates a flowchart of a process 1100 for simulating the structural color of the iris in an example aspect of the present disclosure. A model can be initialized (1110). In a variety of embodiments, the model can be initialized using variables that influence the color of the iris, including the scattering in the stroma layer, determined as described herein with respect to FIGS. 3-10. In many embodiments, the variables can be pre-defined as described below. In a number of embodiments, the melanin ABL ratio $r_A(i,j)$ can be determined based on the inverse intensity of the pixels as darker pixels are often caused by higher concentration of melanin in the ABL. The following variables can be defined for light source wavelengths, although it should be noted that any type of light source, such as infrared, can be utilized as appropriate:

| | |
|---|---|
| $\lambda_r$ [nm] | Light source red wavelength |
| $\lambda_g$ [nm] | Light source green wavelength |
| $\lambda_b$ [nm] | Light source blue wavelength |

The melanin extinction coefficients, including the extinction coefficient of eumelanin $\varepsilon_{eu}(\lambda)[(cm)^{-1}(mg/ml)^{-1}]$ and the extinction coefficient of pheomelanin $\varepsilon_{pheo}(\lambda)[(cm)^{-1}(mg/ml)^{-1}]$ can be defined based on the red, green, and blue variables. In several embodiments, the eumelanin and pheomelanin concentrations fall within a range defined by a high threshold value and a low threshold value. A step size can be defined in order to increase or decrease $c_{eu}$ and $c_{pheo}$ after each ray simulation to minimize $I_{model} - I_{simulated}$.

The eumelanin and pheomelanin absorption coefficients, $\mu_{eu}[cm^{-1}]$ and $\mu_{pheo}[cm^{-1}]$ can be calculated by multiplying the extinction coefficient with concentration. The absorption coefficient indicates the level of absorption per distance for a particular wavelength. For example, the wavelength can be for red, green, blue, infrared, and/or any other wavelength as appropriate.

As described above, a variety of refraction indices are utilized for modeling the path of light rays through various layers of the eye: cornea, aqueous humor, anterior base layer (ABL), stroma, and/or iris pigment epithelium (IPE) can be defined:

| Refractive index | Medium |
|---|---|
| $\eta_{air}$ | Air (sea level) |
| $\eta_{cor}$ | Cornea |

-continued

| Refractive index | Medium |
|---|---|
| $\eta_{ah}$ | Aqueous Humor |
| $\eta_{fib}$ | Fibroblast |
| $\eta_{col}$ | Collagen |
| $\eta_{ipe} = \eta_{base}$ | Iris Pigment Epithelium |
| $\eta_S$ | Stroma |
| $\eta_A$ | Anterior Base Layer |

The following variables can be used to define the thickness (e.g. height) of the iris layers, ABL and stroma.

| Height Iris Layers (mm) | Layer |
|---|---|
| $h_{ABL}$ | ABL |
| $h_{STROMA}$ | Stroma |

The scatter coefficient $\mu_s$ and the anisotropy coefficient g can be calculated using Mie Theory. In several embodiments, the scatter coefficient remains a fixed constant for each wavelength. In many embodiments, the scatter coefficient and/or anisotropy coefficient are automatically recalculated during each modeling loop as described in more detail below. In a variety of embodiments, the following variables can be used to define the scatter coefficient:

| | |
|---|---|
| $\mu_s(\lambda)$ [$\mu m^{-1}$] | Scatter coefficient |
| $\mu_s'(\lambda)$ [$mm^{-1}$] | Reduced scatter coefficient |

It should be noted that any of the above variables can be calculated as described herein and/or predefined values as known in the state of the art can be utilized. Further, more or fewer variables can be used depending on the specific requirements of particular applications of embodiments of the invention.

The ABL ratio can be defined as the fraction of melanin in the ABL over the total melanin in the iris:

$$r_A = \frac{C(melanin)_{abl}}{C(melanin)_{abl} + C(melanin)_{stroma}}$$

for all pixels and/or pixel groups, $r_A(i,j)$, where:

$$r_A(i,j) = \left(\left(\frac{255 - I_r(i,j)}{255}\right) + \left(\frac{255 - I_g(i,j)}{255}\right) + \left(\frac{255 - I_b(i,j)}{255}\right)\right) / 3$$

In many embodiments, the ABL melanin ratio $r_A(i,j)$ remains constant during process 1100.

Light rays from a light source can be simulated (1112). The simulation can include simulate one or more light rays (e.g. photons) at a time from the light source through the iris layers, where they are either absorbed or transmitted out of the iris towards the camera lens. In many embodiments, a Monte Carlo simulation can be used to randomize the simulation. The Monte Carlo simulation can use random numbers $u_i$, for i=1, 2, 3, . . . with values uniformly distributed in the interval [0,1], which are generated on the fly during the simulation. The following random numbers can be used in the simulation:

| Symbol | Usage |
| --- | --- |
| $u_1$ | Fresnel interaction |
| $u_2$ | Diffuse perturbation, polar angle |
| $u_3$ | Diffuse perturbation, azimuthal angle |
| $u_4$ | Absorption test |
| $u_5$ | Attenuation test |
| $u_6$ | Attenuation type |
| $u_7$ | Rayleigh scattering perturbation, polar angle |
| $u_8$ | Rayleigh scattering perturbation, rejection sampling |
| $u_9$ | Rayleigh scattering perturbation, azimuthal angle |
| $u_{10}$ | Scatter position along vector line inside stroma |

It should be noted that more or fewer variables can be used depending on the specific requirements of particular applications of embodiments of the invention.

In a variety of embodiments, a ray can be simulated by start a new ray at boundary of ABL coming from the light source. The ray travels from boundary to boundary. At a boundary one or more of a variety of events can take place, including (1) a reflection event (e.g. the ray is reflected back into the incident layer) and/or (2) a refraction event (e.g. the ray passes through the boundary). In between each boundary one of following events takes place: (1) an absorption event (e.g. the ray end and the simulation of this ray is complete), (2) a scattering event (e.g. the ray changes direction and travels to the next boundary), or (3) neither (e.g. the ray continues in a straight line to the next boundary). In some embodiments, the reflection and refraction events can be diffuse events.

Figure 12:
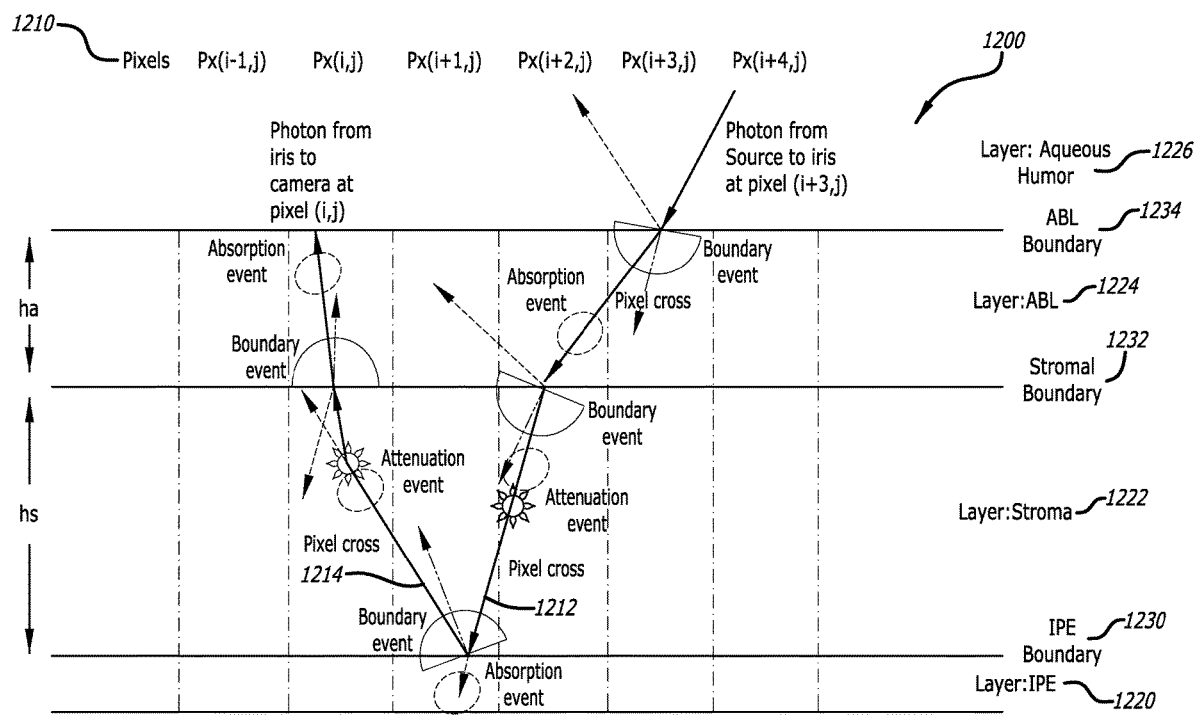
FIG. 12 is a conceptual illustration of simulating rays from a light source in an example aspect of the present disclosure.

An example simulation of a ray traveling through an eye in accordance with embodiments of the invention are described in more detail with respect to FIG. 12. The simulation 1200 starts with a ray 1212 originating at pixel 1210 (i+3,j) in the aqueous humor layer 1226. As the ray 1212 travels through the ABL boundary 1234, a refraction event occurs altering the path of the ray 1212 through the ABL layer 1224, while other rays may be reflected. The ray 1212 passes through the ABL layer 1224 undisturbed, while other rays may be absorbed by melanin. As the ray 1212 travels through the stromal boundary 1232, a second refraction event occurs altering the path of the ray 1212 through the stromal layer 1222, while other rays may be reflected. The ray 1212 passes through the stromal layers 1222 undisturbed while other rays may be scattered by collagen fibrils or absorbed by melanin through an attenuation event. As the ray 1212 interacts with the IPE boundary 1230, the ray 1212 is reflected and continues as reflected ray 1214 through the stromal layer 1222 while other rays may pass through the IPE boundary 1230 and be absorbed in the IPE layer 1220. The reflected ray 1214 passes through the stromal layer 1222 undisturbed, while other rays may be scattered by collagen fibrils or absorbed by melanin through an attenuation event. The reflected ray 1214, as it crosses the stromal boundary 1232, experiences a refraction event that alters the path of the reflected ray 1214 in the ABL layer 1224, while other rays may be reflected. The reflected ray 1214 can pass through the ABL boundary 1234, through the aqueous humor layer 1226, and be detected at pixel 1210 (i,j), while other rays may be absorbed by melanin.

Melanin concentrations can be calculated (1114). The melanin concentrations can be determined based on the number and/or intensity of the rays that exit the iris as described herein. Based on the rays, the melanin coefficients $c_{eu}(i,j)$ and $c_{pheo}(i,j)$ can be calculated and/or updated for all pixels (i,j) where the ray traveled. For example, for each simulated ray that exits the iris towards the camera sensor at pixel (x,y), the difference ($I_{reality}(x,y)-I_{simulated}(x,y)$) can be minimized by increasing or decreasing the melanin concentrations $c_{eu}(i,j)$ and $c_{pheo}(i,j)$ where pixels (i,j) are all the pixels through which this particular ray traveled.

The simulation of light rays and calculation of melanin coefficients can be repeated (1116) until the simulation reaches a desired number of iterations (e.g. a threshold number of rays have been simulated) and/or a desired accuracy is reached. In many embodiments, the desired accuracy is determined based on the amount of change between simulations is below a threshold value). The number of simulated rays can be between a minimum and/or a maximum threshold. For example, the minimum threshold may be 10,000 rays and the maximum threshold may be 10,000,000 rays, although any number of rays can be simulated as appropriate. If an accuracy threshold has been reached (1116), iris color data can be calculated (1118). If an accuracy threshold has not been reached (1116), the process 1100 returns to step 1112. Iris color data can be calculated for any lighting environment (1118). The iris color data can be calculated for any lighting environment based on the calculated melanin concentrations as described herein.

Although the process 1100 is described with reference to the flowchart illustrated in FIG. 11, it will be appreciated that many other methods of performing the acts associated with the process 1100 may be used. For example, the order of some of the blocks may be changed, certain blocks may be combined with other blocks, one or more blocks may be repeated, and some of the blocks described are optional. The process 1100 may be performed by processing logic that may include hardware (circuitry, dedicated logic, etc.), software, or a combination of both.

The following is an example algorithm for simulating a light ray as described with respect to FIG. 11 and shown in FIG. 12. The simulation can run under one or both of the following conditions:

```
While (number of rays simulated < R_maxsource) # certain amount
of rays from the light source
While (number of rays reached sensor at pixel (i,j) > R_minsensor) #
until the minimum amount of rays have reached each
sensor pixel
Pick random wavelength λ ∈ {R, G, B} # or rotate through each
one
Pick random iris pixel (i,j) # as incident light ray starting
point
Retrieve vector v(α,β) at pixel (i,j) # pre-calculated incident
light vector at pixel(i,j)
# α can be a polar angle, β can be an azimuthal angle
```

Every new ray encounters ABL boundary from the Aqueous Humor first

```
CurrentLayer = AH
GoToNextBoundary(v) #ray goes along vector v to ABL
Boundary
```

If at any boundary, decide whether to reflect or transmit the ray first. A diffuse perturbation can be applied when the ray (re)enters the ABL and Stromal Layers. The ray successfully completes when the ray (re)enters the aqueous humor layer. The ray ends when the ray enters the IPE layer. Pseudocode 1300 conceptually showing this calculation is shown in FIG. 13A.

When entering the ABL layer, the ray can either be absorbed (and the ray ends) or be transmitted, where the ray continues in a straight line to the next boundary). When entering the Stromal layer, the ray can be absorbed (and the ray ends), be scattered (change the direction of the ray and then continue in a straight line to the next boundary), or be transmitted (continue the ray in an undisturbed straight line to the next boundary). Pseudocode 1320 conceptually showing this calculation is shown in FIG. 13B.

The new direction $v(\alpha_R, \beta_R)$ using for a ray can be determined using a Rayleigh scattering phase function. Pseudocode 1340 conceptually showing this calculation is shown in FIG. 13C. The distance the ray travels within each pixel column that it traverses in the ABL and Stromal layer can be measured. Pseudocode 1360 conceptually showing this calculation is shown in FIG. 13D.

In many embodiments, a Fresnel test can be performed to determine if a ray should be reflected or transmitted (e.g. refracted) through a boundary. As each layer has a different refractive index, either reflection or transmission can occur at all boundaries. This reflection or transmission can be calculated based on a reflection coefficient R. $\vartheta_i$ is incident angle from the surface normal. If a boundary is flat, $\vartheta_i = \alpha$ (polar angle) and $$R = \frac{R_{perpendicular} + R_{parallel}}{2} = \frac{\tan^2(\vartheta_i - \vartheta_t)}{2 \cdot \tan^2(\vartheta_i + \vartheta_t)} + \frac{\sin^2(\vartheta_i - \vartheta_t)}{2 \cdot \sin^2(\vartheta_i + \vartheta_t)},$$

$$\text{where } \vartheta_t = \sin^{-1}\left(\frac{\eta_i \cdot \sin\vartheta_i}{\eta_t}\right)$$

If $u_1 \leq R$ then ray is reflected, else ray is transmitted.

The angle of reflection/transmission can be determined. When a ray enters (through reflection or transmission) either the ABL or Stromal Layer, the ray can be diffusely perturbed due to the internal arrangement of the tissues. In order to account for this effect, a warping function based on the cosine distribution as follows for the resulting diffused vector $\underline{v}_d(\alpha_d, \beta_d)$:

$\underline{v}_d(\alpha_d, \beta_d) = (\cos^{-1}((1-u_2)^{1/2}), 2\pi \cdot u_3)$ where $\alpha_d$ is polar angle and $\beta_d$ is azimuthal angle In several embodiments, the cosine perturbation can include a bias towards $$\vartheta_t = \sin^{-1}\left(\frac{\eta_i \cdot \sin\vartheta_i}{\eta_t}\right).$$

In many embodiments this is determined based on the average of two angles:

$$\left(\frac{\alpha_d + \vartheta_t}{2}, \frac{\beta_d + \beta_i}{2}\right)$$

where $\beta_i$ is the incident azimuthal angle.

Rejection sampling can be used to prevent the perturbed direction of propagation that invalidates the result of the Fresnel test performed at a particular boundary. For example, the Fresnel test can indicate a refraction and the ensuing diffuse perturbation using cosine distribution is rejected if it makes the path of the ray into a reflection.

--- if (fresnel$_{test}$ = transmit) AND $\underline{v}_d \cdot \underline{n}$
 $\geq 0$, then reject $\underline{v}_d$ resample $u_2$ and $u_3$, and find new $\underline{v}_d$
if (fresnel$_{test}$ = reflect) AND $\underline{v}_d \cdot \underline{n}$
 $\leq 0$, then reject $\underline{v}_d$: resample $u_2$ and $u_3$, and find new $\underline{v}_d$.
End function

---

When a ray is traversing either the ABL, possible absorption due to the presence of eumelanin and pheomelanin pigments can be determined. In a variety of embodiments, the absorption coefficient can be calculated for all pixels along length based on the average of absorption coefficients of eu- and pheomelanin. The probability of absorption can be calculated as follows:

---

For all pixels(i,j) along $l_{bb}$
 $\mu_{a,ABL} = \mu_{a,ABL} + (\varepsilon_{eu}(\lambda) \cdot c_{eu}(i,j) \cdot r_A + \varepsilon_{pheo}(\lambda) \cdot c_{pheo}(i,j) \cdot r_A) / 2$
$P_{\mu_a}(\lambda) = 1 - \exp(-\mu_{a,ABL} \cdot l_{bb})$ # determine probability of absorption
$f(P_{\mu_a}(\lambda) \leq u_4$, thenAbsorbTest = "Yes", else AbsorbTest = "No" # decide whether to absorb or transmit

---

When the ray travels through the stroma, it may be absorbed, scattered, or transmitted undisturbed by the tissue in the stroma. The attenuation type, i.e. either absorbed, scattered or transmitted, can be modeled based on the scatter probability, the absorption probability, and the distance that the ray travels through the stroma. In many embodiments, the absorption coefficient can be calculated for all pixels along length, taking average of absorption coefficients of eu- and pheomelanin:

For all pixels (i,j) along $l_{bb}$ $\mu_{a,STROMA}(\lambda) = \mu_{a,STROMA}(\lambda) + (\varepsilon_{eu}(\lambda) \cdot c_{eu}(i,j) \cdot (1-r_A) + \varepsilon_{pheo}(\lambda) \cdot c_{pheo}(i,j) \cdot (1-r_A))/2$ Attenuation coefficient can be calculated based on the sum of absorption and scatter coefficients:

$\mu(\lambda) = \mu_{a,stroma}(\lambda) + \mu_s(\lambda)$ where $\mu_s(\lambda)$ is a constant as described herein.

The attenuation probability can be calculated as:

$P_\mu(\lambda) = 1 - \exp(-\mu(\lambda) \cdot l_{bb})$

The absorption probability can be calculated as:

$$P_{\mu_{a,stroma}}(\lambda) = \frac{\mu_{a,stroma}(\lambda)}{\mu(\lambda)}$$

The attenuation results can be determined by:

--- if($u_5 > P_\mu(\lambda)$),then AttenuationTest = "Transmit"  # neither absorption nor scattering
  else
if($u_6 \leq P_{\mu_{a,stroma}}(\lambda)$),then AttenuationTest = "Absorb"  # ray is absorbed
  else
  AttenuationTest = "Scatter"

---

When the ray complete its path, the ray exits the ABL towards the camera pixel. At this stage, the ray can be evaluated for all the pixels (i,j) that the ray traversed and a determination to either increase or decrease $c_{eu}(i,j)$ and $c_{pheo}(i,j)$ can be made. In many embodiments, increasing or decreasing $c_{eu}(i,j)$ and $c_{pheo}(i,j)$ is made to adjust the frequency of the type of ray to occur more or less often in future simulations.

---

$S_\lambda(x,y) = S_\lambda(x,y) + 1/(R_{maxsource})$ # simulated value at this wavelength at ray exit pixel (x,y)
$\delta_\lambda(x,y) = R_\lambda(x,y) - S_\lambda(x,y)$ # delta is difference at this wavelength and pixel (x,y) between real captured image and simulated image The ray-occurrence probability of this ray can be calculated as:

$P_{ray}(x, y) =$ $P$(along ray's path in $ABL$|not| absorbed by eumelanin OR pheomelanin)

AND $P$(along ray's path in Stroma

|not|absorbed by eumelanin OR pheomelanin)

$P_{not\,absorbed,ABL}(x, y) = \sum_{i,j} (\exp(-r_{eu}(i, j) \cdot \varepsilon_{eu}(\lambda) \cdot l(i, j) \cdot c_{eu}(i, j)) +$ $\exp(-r_{pheo}(i, j) \cdot \varepsilon_{pheo}(\lambda) \cdot l(i, j) \cdot c_{pheo}(i, j)))$ $P_{not\,absorbed,Stroma}(x, y) = \sum_{i,j} (\exp(-(1 - r_{eu}(i, j)) \cdot \varepsilon_{eu}(\lambda) \cdot l(i, j) \cdot c_{eu}(i, j)) +$ $\exp(-(1 - r_{pheo}(i, j)) \cdot \varepsilon_{pheo}(\lambda) \cdot l(i, j) \cdot c_{pheo}(i, j)))$ $P_{ray}(x, y) = P_{not\,absorbed,ABL}(x, y) \cdot P_{not\,absorbed,Stroma}(x, y)$ For a particular pixel, when the real intensity is higher than the simulated intensity, the ray-occurrence probability can be increased, which corresponds to a melanin concentration decrease.

---

If($R(x,y) \geq S(x,y)$),then
per pixel (i,j), decrease eumelanin concentration by 0 or 1 increment and/
or decrease pheomelanin concentration by 0 or 1 increment.
    There are 2 {0,1} x 2 {$c_{eu}$, $c_{pheo}$} x number of pixels(i,j) combinations
        For all combinations
           $c_{eu}(i,j) = c_{eu}(i,j) - \{0,1\}$ eu increment
           $c_{pheo}(i,j) = c_{pheo}(i,j) - \{0,1\}$ pheo increment
           Recalculate $P_{ray}(x,y)$ with the changed $c_{eu}$ and $c_{pheo}$
    if $P_{ray}(x,y) > P_{max}(x,y)$,then # find highest P_ray(x,y)
           $P_{max}(x,y) = P_{ray}(x,y)$, and
           remember the $c_{eu}(i,j)$ and $c_{pheo}(i,j)$

---

To decrease the ray-occurrence probability, the concentration of melanin can be increased.

---

Per pixel (i,j),increase eumelanin concentration by 0 or 1 increment and
/or increase pheomelanin concentration by 0 or 1 increment.
    There are 2 {0,1}x 4 {$c_{eu,abl}$, $c_{pheo,abl}$, $c_{eu,stroma}$, $c_{pheo,stroma}$}x number of pixels (i,j)
        combination. For all combinations:
           $c_{eu}(i,j) = c_{pheo}(i,j) + \{0,1\}$ # eu increment
           $c_{pheo}(i,j) = c_{pheo}(i,j) + \{0,1\}$ # pheo increment
           Recalculate $P_{ray}(x,y)$ with the changed $c_{eu}$ and $c_{pheo}$
    If $P_{ray}(x,y) < P_{max}(x,y)$, then # find lowest P_ray(x,y)
           $P_{max}(x,y) = P_{ray}(x,y)$; and
        store the $c_{eu}(i,j)$ and $c_{pheo}(i,j)$

---

In a variety of embodiments, the concentration of melanin in the pixel set (i,j) (e.g.) the pixels through which the ray traversed to before exiting at pixel (x,y)) can be increased or decreased to a level such that $\delta_\lambda(x,y)$ approximates zero.

It will be appreciated that all of the disclosed methods and procedures described herein can be implemented using one or more computer programs, components, and/or program modules. These components may be provided as a series of computer instructions on any conventional computer readable medium or machine-readable medium, including volatile or non-volatile memory, such as RAM, ROM, flash memory, magnetic or optical disks, optical memory, or other storage media. The instructions may be provided as software or firmware and/or may be implemented in whole or in part in hardware components such as ASICs, FPGAs, DSPs, or any other similar devices. The instructions may be configured to be executed by one or more processors, which when executing the series of computer instructions, performs or facilitates the performance of all or part of the disclosed methods and procedures. As will be appreciated by one of skill in the art, the functionality of the program modules may be combined or distributed as desired in various aspects of the disclosure.

Although the present disclosure has been described in certain specific aspects, many additional modifications and variations would be apparent to those skilled in the art. In particular, any of the various processes described above can be performed in alternative sequences and/or in parallel (on the same or on different computing devices) in order to achieve similar results in a manner that is more appropriate to the requirements of a specific application. It is therefore to be understood that the present disclosure can be practiced otherwise than specifically described without departing from the scope and spirit of the present disclosure. Thus, embodiments of the present disclosure should be considered in all respects as illustrative and not restrictive. It will be evident to the annotator skilled in the art to freely combine several or all of the embodiments discussed here as deemed suitable for a specific application of the disclosure. Throughout this disclosure, terms like "advantageous", "exemplary" or "preferred" indicate elements or dimensions which are particularly suitable (but not essential) to the disclosure or an embodiment thereof, and may be modified wherever deemed suitable by the skilled annotator, except where expressly required. Accordingly, the scope of the invention should be determined not by the embodiments illustrated, but by the appended claims and their equivalents.

What is claimed is:

1. A computer-implemented method, comprising:
obtaining refraction data;
obtaining mesh data;
generating aligned model data by aligning the refraction data and the mesh data;
calculating refraction points in the aligned model data;
calculating melanin information for the aligned model data based on the refraction points for iris pixels in the aligned model data; and
calculating an approximated iris color based on the refraction points, a melanin absorption coefficient, an iris stroma scattering coefficient, an anisotropy of a scattering phase function, and the aligned model data.

2. The computer-implemented method of claim 1, further comprising calculating the refraction points based on multiple lighting conditions.

3. The computer-implemented method of claim 1, further comprising:
calculating a melanin concentration based on the refraction points and the aligned model data; and
calculating the approximated iris color based on the melanin concentration.

4. The computer-implemented method of claim 3, further comprising calculating the melanin concentration based on at least one predetermined variable.

5. The computer-implemented method of claim 1, further comprising calculating the refraction points based on a Monte Carlo simulation of a plurality of light rays.

6. The computer-implemented method of claim 1, wherein the refraction points comprise a boundary layer between layers in an iris.

7. A computer-implemented method, comprising:
obtaining refraction data;
obtaining mesh data;
generating aligned model data by aligning the refraction data and the mesh data;
calculating refraction points in the aligned model data; and
calculating an approximated iris color based on the refraction points, a melanin absorption coefficient, an iris stroma scattering coefficient, an anisotropy of a scattering phase function, and the aligned model data by calculating a Mie scattering.

8. The computer-implemented method of claim 7, further comprising calculating the refraction points based on multiple lighting conditions.

9. The computer-implemented method of claim 7, further comprising:
calculating a melanin concentration based on the refraction points and the aligned model data; and
calculating the approximated iris color based on the melanin concentration.

10. The computer-implemented method of claim 9, further comprising calculating the melanin concentration based on at least one predetermined variable.

11. The computer-implemented method of claim 7, further comprising calculating the refraction points based on a Monte Carlo simulation of a plurality of light rays.

12. The computer-implemented method of claim 7, wherein the refraction points comprise a boundary layer between layers in an iris.

13. An apparatus, comprising:
a processor; and
a memory storing instructions that, when read by the processor, cause the apparatus to:
obtain refraction data;
obtain mesh data;
generate aligned model data by aligning the refraction data and the mesh data;
calculate refraction points in the aligned model data;
calculate melanin information for the aligned model data based on the refraction points for iris pixels in the aligned model data; and
calculate an approximated iris color based on the refraction points, a melanin absorption coefficient, an iris stroma scattering coefficient, an anisotropy of a scattering phase function, and the aligned model data.

14. The apparatus of claim 13, wherein the instructions, when read by the processor, further cause the apparatus to calculate the refraction points based on multiple lighting conditions.

15. The apparatus of claim 13, wherein the instructions, when read by the processor, further cause the apparatus to:
calculate a melanin concentration based on the refraction points and the aligned model data; and
calculate the approximated iris color based on the melanin concentration.

16. The apparatus of claim 13, wherein the refraction points are calculated based on a Monte Carlo simulation of a plurality of light rays.

17. The apparatus of claim 13, wherein the refraction points comprise a boundary layer between layers in an iris.

* * * * *